(12) United States Patent
Goddard, III et al.

(10) Patent No.: US 9,272,051 B2
(45) Date of Patent: Mar. 1, 2016

(54) METHODS AND SYSTEMS FOR MODULATING HORMONES AND RELATED METHODS, AGENTS AND COMPOSITIONS

(71) Applicants: William A. Goddard, III, Pasadena, CA (US); Mark Menna, Los Angeles, CA (US); Stephen Pandol, Los Angeles, CA (US); Ravinder Abrol, Arcadia, CA (US)

(72) Inventors: William A. Goddard, III, Pasadena, CA (US); Mark Menna, Los Angeles, CA (US); Stephen Pandol, Los Angeles, CA (US); Ravinder Abrol, Arcadia, CA (US)

(73) Assignees: California Institute of Technology, Pasadena, CA (US); The Regents of the University of California, Oakland, CA (US); The United States Government Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/320,159

(22) Filed: Jun. 30, 2014

(65) Prior Publication Data

US 2014/0364387 A1  Dec. 11, 2014

Related U.S. Application Data

(63) Continuation of application No. 13/163,638, filed on Jun. 17, 2011, now Pat. No. 8,796,233.

(60) Provisional application No. 61/397,940, filed on Jun. 17, 2010.

(51) Int. Cl.
| | | |
|---|---|---|
| *A61K 31/513* | (2006.01) | |
| *A61K 31/704* | (2006.01) | |
| *A61K 31/352* | (2006.01) | |
| *A61K 31/122* | (2006.01) | |
| *A61K 31/12* | (2006.01) | |
| *A61K 31/353* | (2006.01) | |
| *A61K 47/48* | (2006.01) | |
| *A61K 31/10* | (2006.01) | |
| *A61K 31/167* | (2006.01) | |
| *A61K 31/205* | (2006.01) | |
| *A61K 31/365* | (2006.01) | |
| *A61K 31/4375* | (2006.01) | |
| *A61K 31/4745* | (2006.01) | |
| *A61K 31/7016* | (2006.01) | |
| *G01N 33/566* | (2006.01) | |
| *A61K 31/17* | (2006.01) | |

(52) U.S. Cl.
CPC ............ *A61K 47/4823* (2013.01); *A61K 31/10* (2013.01); *A61K 31/12* (2013.01); *A61K 31/122* (2013.01); *A61K 31/167* (2013.01); *A61K 31/17* (2013.01); *A61K 31/205* (2013.01); *A61K 31/352* (2013.01); *A61K 31/353* (2013.01); *A61K 31/365* (2013.01); *A61K 31/4375* (2013.01); *A61K 31/4745* (2013.01); *A61K 31/513* (2013.01); *A61K 31/704* (2013.01); *A61K 31/7016* (2013.01); *G01N 33/566* (2013.01)

(58) Field of Classification Search
CPC . A61K 47/4823; A61K 31/513; A61K 31/17; A61K 31/704; A61K 31/353; A61K 31/122; A61K 31/4375; A61K 31/10; A61K 31/12; A61K 31/352
USPC .............................. 514/34, 274, 57, 456, 678
See application file for complete search history.

(56) References Cited

U.S. PATENT DOCUMENTS

| | | | | |
|---|---|---|---|---|
| 6,500,459 B1 * | 12/2002 | Chhabra et al. | ............... | 424/474 |
| 7,465,550 B2 * | 12/2008 | Zuker et al. | ..................... | 435/7.1 |
| 8,796,233 B2 * | 8/2014 | Goddard et al. | ................ | 514/33 |
| 2003/0153512 A1 * | 8/2003 | Hergenhahn et al. | ........... | 514/25 |
| 2009/0022806 A1 * | 1/2009 | Mousa et al. | ................. | 424/489 |

FOREIGN PATENT DOCUMENTS

| | | |
|---|---|---|
| WO | 2004081023 A1 | 9/2004 |
| WO | 2010033580 A2 | 3/2010 |
| WO | 2010049302 A1 | 5/2010 |

OTHER PUBLICATIONS

Polyox, The Dow Chemical Company, Form No. 326•00001 •0302 AMS pp. 1-24, Mar. 2002.*
JP Notification of Reasons for Refusal mailed May 26, 2015 for JP Application No. 2013-515572.

* cited by examiner

*Primary Examiner* — Mark Shibuya
*Assistant Examiner* — Yih-Horng Shiao
(74) *Attorney, Agent, or Firm* — The Law Offices of Leslie B. Overman

(57) ABSTRACT

Provided herein are bitter taste receptor ligands, related agents, combinations, compositions, methods and systems for modulating release of a metabolic hormone in vitro or in vivo from cells of the GI tract of an individual.

5 Claims, 21 Drawing Sheets

```
hβ1AR    - - - - M G A E L L S Q Q W E A G M S L L M A L V V L L I V A G N V L V I A A I G S T - - - Q R L
PAV      M L T L T R I R T V S Y E V R S T F L F I S V L E F A V G F L T N A F V F L V N F W D V V K R Q P L
AVI      M L T L T R I R T V S Y E V R S T F L F I S V L E F A V G F L T N A F V F L V N F W D V V K R Q A L
AAI      M L T L T R I R T V S Y E V R S T F L F I S V L E F A V G F L T N A F V F L V N F W D V V K R Q A L
PVV      M L T L T R I R T V S Y E V R S T F L F I S V L E F A V G F L T N A F V F L V N F W D V V K R Q P L hβ1AR    Q         T L T N L F I T S L A C A D L V V G L L V V P F G A T L V V R G T W L W - - - G S F L C E L
PAV      S N S D C V L L C L S I S R L F L H G L L F L S A I Q L T H F Q K L S E P L N H S Y Q A I I M L W M
AVI      S N S D C V L L C L S I S R L F L H G L L F L S A I Q L T H F Q K L S E P L N H S Y Q A I I M L W M
AAI      S N S D C V L L C L S I S R L F L H G L L F L S A I Q L T H F Q K L S E P L N H S Y Q A I I M L W M
PVV      S N S D C V L L C L S I S R L F L H G L L F L S A I Q L T H F Q K L S E P L N H S Y Q A I I M L W M hβ1AR    W T S L D V L C V T A S I E T L C V I A I D R Y L A I T S P F R Y Q - - S L M T R A R A K V I I C T
PAV      I A N Q A N L W L A A C L S L L Y C S K L I R F S H T F L I C L A S W V S R K I S Q M L L G I I L C
AVI      I A N Q A N L W L A A C L S L L Y C S K L I R F S H T F L I C L A S W V S R K I S Q M L L G I I L C
AAI      I A N Q A N L W L A A C L S L L Y C S K L I R F S H T F L I C L A S W V S R K I S Q M L L G I I L C
PVV      I A N Q A N L W L A A C L S L L Y C S K L I R F S H T F L I C L A S W V S R K I S Q M L L G I I L C hβ1AR    V W A I S A L V S F L P I M M H W W R D E D P Q A L K C Y Q D P G C C D F V T N R A Y A I A S S I I
PAV      S C I C T V L C V W C F F S R P H F T V T T V L F M N N N T R L N W Q I K D L N L F Y S F L F C Y L
AVI      S C I C T V L C V W C F F S R P H F T V T T V L F M N N N T R L N W Q I K D L N L F Y S F L F C Y L
AAI      S C I C T V L C V W C F F S R P H F T V T T V L F M N N N T R L N W Q I K D L N L F Y S F L F C Y L
PVV      S C I C T V L C V W C F F S R P H F T V T T V L F M N N N T R L N W Q I K D L N L F Y S F L F C Y L hβ1AR    S F Y I P L L I M I F V A L R V Y R E A K E Q I R K I D R A S K R K R - V M L M - - - R E H K A L K
PAV      W S V P P F L L F L V S S G M L T V S L G R H M R T M K V Y T R N S R D P S L E A H I K A L K S L V
AVI      W S V P P F L L F L V S S G M L T V S L G R H M R T M K V Y T R N S R D P S L E A H I K A L K S L V
AAI      W S V P P F L L F L V S S G M L T V S L G R H M R T M K V Y T R N S R D P S L E A H I K A L K S L V
PVV      W S V P P F L L F L V S S G M L T V S L G R H M R T M K V Y T R N S R D P S L E A H I K A L K S L V

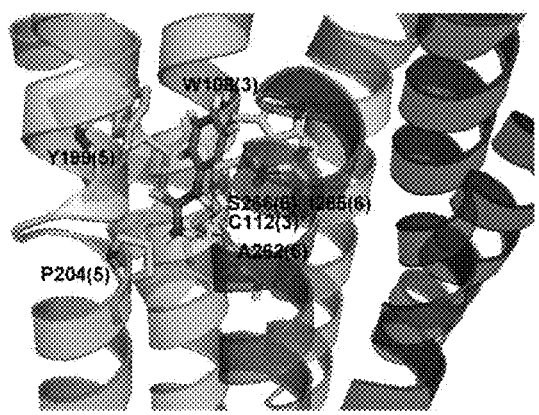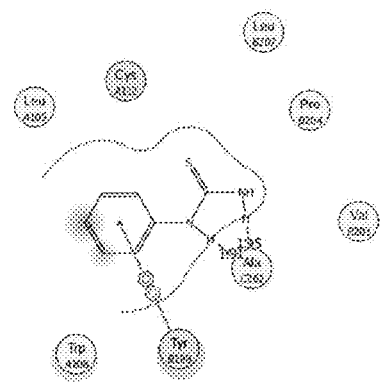
a
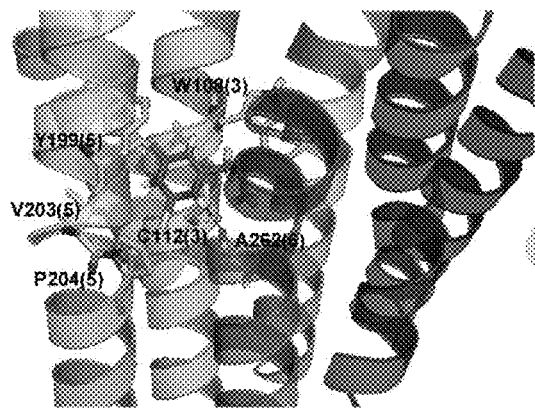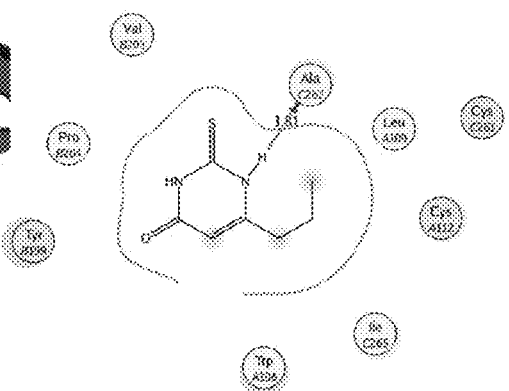
b
FIG. 8A-8B

A.

B.

```
* HYDROPHOBIC CENTER                    *
h TM 1    13   43        EVRSTFLFISVLEFAVGFLTNAFVFLVNFWD
r TM 1    13   43        EAKISFLFLSVVEFAVGIMANAFIVLVNFWD
h TM 2f   83   54        KQFHTLQIASLFLLGHLFLRSISLCLLVCD
r TM 2f   82   54        QFCALQIADLLLLGQLFLRTISLCLLAID
h TM 3    90   133      HSYQAIIMLWMIANQANLWLAACLSLLYCSKLIRFSHTFLICLA
r TM 3    94   133       AILTLWMSANQVSLWLAACLSLLYCAKIVRFSHTFPLHLA
h TM 4f   165  138           RSFFCWVCLVTCICSCLIIGLLMQSIKR
r TM 4f   161  138            DWLCLATCVGSFLLAVLIMQLFRR
h TM 5    188  221         DLNLFYSFLFCYLWSVPPFLLFLVSSGMLTVSLG
r TM 5    187  220         KLNFFYSFVFCNVGSVPPSLVFLISSGVLVISLG
h TM 6f   269  247              LPVSIFAACSSIVFFCFFSVLSK
r TM 6f   268  243            LPISILAACFSVVYFCLFSVLFIIAR
h TM 7    280  300               MVCVGIMAACPSGHAAILISG
r TM 7    279  299               MVCIGMMAACPSGHAAILISG
* HYDROPHOBIC CENTER                    *
```

FIG. 21

METHODS AND SYSTEMS FOR MODULATING HORMONES AND RELATED METHODS, AGENTS AND COMPOSITIONS

CROSS REFERENCE TO RELATED APPLICATIONS

This application is a continuation of U.S. application Ser. No. 13/163,638 filed on Jun. 17, 2011, which in turn, claims priority to U.S. Provisional Application entitled "Receptors, agents, treatment of diseases and conditions" Ser. No. 61/397,940 filed on Jun. 17, 2010, the disclosure of each of which is incorporated herein by reference in its entirety.

STATEMENT OF GOVERNMENT GRANT

This invention was made with government support under Grant No. AT003960 awarded by the National Institutes of Health and the U.S. Department of Veterans Affairs. The government has certain rights in the invention.

FIELD

The present disclosure relates to methods and systems for modulating hormones and related methods, ligands, agents and compositions.

BACKGROUND

Hormones are chemical substances often identified as mediators, typically released by a cell or a gland in one part of an organism to act as a chemical messenger to other parts of the organism.

Various biological processes and in particular metabolic processes are associated to the release of hormones in an organism. In particular various metabolic hormones (e.g. peptide based hormones) affect and regulate the metabolism networks of cells and/or organs in an individual.

However, controlling hormones production and in particular modulation of hormone release in connection with treatment of various conditions in the individual has been challenging.

SUMMARY

Provided herein, are methods, systems and compositions which allow in several embodiments, modulating the release of metabolic hormones and related biological processes, identifying ligands capable of performing that modulation and controlling the modulation. In particular provided herein are agents, compositions methods and systems for modulating release of metabolic hormones and controlling related biological process, including agents, compositions methods and systems that are suitable for treating metabolic conditions.

According to a first aspect, methods, systems and compositions for modulating release of a metabolic hormone and a related biological process in an individual are described. The method comprises administering to the individual one or more GI bitter taste receptor ligands selected from PTU, PTC, denatonium benzoate, Glycyrrhizic acid amomonium salt, Epigallocatechin gallate, Hyperforin, Berberine chloride, Coptisine Chloride Allylsulfide, Rottlerin, Curcumin, Ellagic acid, Embelin, and/or a derivative thereof, in an effective amount to allow binding to the one or more GI bitter taste receptors in the individual, the binding resulting in modulating the release of the metabolic hormone and related biological process, the metabolic hormone selected from the group consisting of GLP-1, PYY and CCK. The system comprises at least two of one or more GI bitter taste receptor ligands for simultaneous combined or sequential use in the method for modulating hormone release herein described. The composition comprises one or more ligands able to bind one or more target GI bitter taste receptor upon administering to the individual together with a suitable vehicle.

According to a second aspect, a bitter taste agent for modulating a target bitter taste receptor, and in particular a GI bitter taste receptor, in an individual, and related methods, systems and compositions are described. The bitter taste agents are based on a combination of a bitter taste receptor ligand and a complementary molecule configured for interfering with systemic absorption and release of the bitter taste receptor ligand. In particular, the bitter taste agent can comprise a bitter taste receptor ligand conjugated with a complementary molecule wherein the ligand has a first portion and a second portion. In the bitter taste agent, the first portion of the bitter taste receptor ligand is active with respect to binding of bitter taste ligand to the bitter taste receptor and the second portion is passive with respect to binding of bitter taste ligand to the bitter taste receptor. In the bitter taste agent, the complementary molecule is attached to the ligand in the second portion of the ligand and the resulting bitter taste agent is configured to present the first portion for binding to the bitter taste receptor. The method comprises administering an effective amount of the bitter taste agent to the individual. The composition comprises one or more bitter taste receptor ligands and at least one complementary molecule. The system comprises at least two of one or more bitter taste receptor ligands and a complementary molecule for simultaneous combined or sequential use in providing a bitter taste agent and/or in the method to modulate hormone release herein described.

According to third aspect, a method and systems to identify a biological response associated to activation of a bitter tastant receptor in a cell, and in particular a cell of the GI tract, are described. The method comprises contacting the cell with a bitter tastant receptor ligand selected from PTU, PTC, denatonium benzoate, Glycyrrhizic acid amomonium salt, Epigallocatechin gallate, Hyperforin, Berberine chloride, Coptisine Chloride Allyl sulfide, Rottlerin, Curcumin, Ellagic acid, Embelin, and/or a derivative thereof to allow binding of the ligand to the bitter tastant receptor and detecting the biological response in the cell following the contacting. In some embodiments the method further comprises comparing the detected biological response to a reference biological response to characterize the biological response. The system comprises at least two of one or more bitter taste receptor ligands and a cell, for simultaneous combined or sequential use in the method to identify a biological response herein described.

According to a fourth aspect, methods, systems and compositions for screening candidate ligands to identify a GI bitter taste receptor ligand capable of modulating release of metabolic hormones associated to the GI system, which in some embodiments is performed based on the specific locations of a target cell in the GI system and specific bitter receptors expressed by the target cell. The method comprises identifying a bitter taste receptor that is expressed in the target cell in the GI system, predicting the structure of the GI bitter tastant receptor, identifying a candidate ligand that binds to this receptor based on the predicted structure, testing the ligand in a bitter taste receptor activation assay, and then testing the effect of that ligand on the modulation of at least one of the metabolic hormones associated to the GI system.

According to a fifth aspect, a method to modulate a hormone release from a cell comprising inducing a specific conformation of a GI bitter tastant receptor through binding of a GI bitter taste receptor ligand, the specific conformation being at least one of a plurality of active conformations of the bitter tastant receptor, detecting increase or decrease of a hormone release from a cell following the inducing, and modulating said increase or decrease through action of the GI bitter taste receptor ligand. In some embodiment, the inducing is preceded by identifying the GI bitter taste receptor ligand.

According to a sixth aspect, bitter taste receptor ligands, agents, and related methods and systems to treat or prevent in an individual a condition associated with a metabolic hormone are described. The method comprises administering to the individual one or more GI bitter taste receptor ligands selected from PTU, PTC, denatonium benzoate or a derivative thereof, in a therapeutically effective amount to modulate metabolic hormone GLP-1, PYY and/or CCK. The system comprises at least two of a bitter taste receptor ligands or agents herein described for simultaneous combined or sequential use in the method to treat or prevent in an individual a conditions associated with a metabolic hormone herein described.

The methods, systems and compositions herein described allow in several embodiments modulating the activity of GI bitter taste receptors, modulating secretion and systemic release of metabolic hormones and modulating related metabolic conditions as well as other biological processes, including treating metabolic diseases.

The methods and compositions herein described can be used in connection with applications wherein modulating activity of GI and intestinal bitter taste receptors is desired, including but not limited to medical application, biological analysis, food processing, taste/flavor modulation, nutrition, nutraceutical applications, and diagnostics including but not limited to clinical applications.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples section, serve to explain the principles and implementations of the disclosure.

FIG. 1 shows sequence alignment against the β1 Adrenergic Receptor (h β 1 AR) (SEQ ID NO: 1) for TAS2R38 bitter taste receptor variants hTAS2R38$_{PAV}$ (SEQ ID NO: 2), hTAS2R38$_{AAI}$ (SEQ ID NO: 4), hTAS2R38$_{PVV}$ (taster) (SEQ ID NO: 5) and hTAS2R38$_{AVI}$ (nontaster) (SEQ ID NO: 3).

FIG. 21 shows the TM regions for rat and human TAS2R38 taste receptors (SEQ ID NO: 13 to SEQ ID NO: 26).

DETAILED DESCRIPTION

Figure 2:
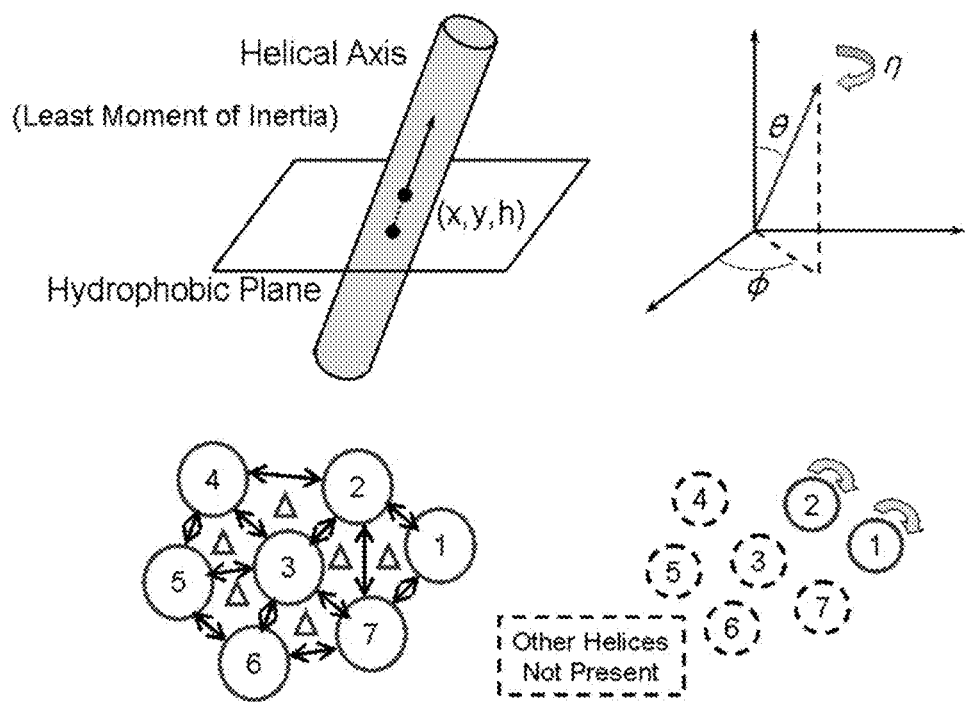
FIG. 2 shows the coordinate system used to describe the orientation of the seven helices in a GPCR bundle. Double arrows connect nearest neighbor helix pairs that are sampled independently in the BiHelix procedure. The BiHelix procedure is highlighted using helices 1 and 2 to show that when the conformations for this helix pair are sampled, other helices are not present.

Described herein are methods, systems, and compositions for modulating release of metabolic hormones, related metabolic conditions and other related biological processes, including treating metabolic diseases in an individual.

The term "modulate" or "modulation" as used herein with respect to an activity of cell membrane receptors and/or a quantifiable biological event, such as release of hormones, indicates the process of interfering with the activity or biological event. Examples of interfering comprise increasing, decreasing or maintaining the activity and/or quantifiable event. For example modulation of the activity of a cell receptor such as GPCRs can be performed by increasing the activity of the GPCR by converting the GPCR into one of the active conformations which can be performed for example following interaction of a ligand with a GPCR or even a single mutation in a GPCR. Analogously, maintaining or decreasing activity can be performed respectively by maintaining or converting the GPCR into the inactive conformation, which can also be performed through interaction of a ligand or various mutations of the GPCRS. Similarly, increasing, decreasing or maintaining of a biological event such as release of a biological hormone, can be performed by activation or deactivation of various intercellular and/or intracellular pathways that result from activation of a GPCR, which can performed by operating on the GPCRs activity. Detection of a modulating activity can be performed for example through detection of changes in basal activity and/or basal quantifiable event, for example biological and/or chemical indicators associated to the activity and/or the event to be modulated. A skilled person is able to identify the proper biological and/or chemical indicators associated to the event of choice using technique and methods known to a skilled person and/or identifiable upon reading of the present disclosure.

The term "hormones" as used herein indicates a chemical substance often identified as mediator, which is typically released by a cell or a gland in one part of an organism to act as a chemical messenger to other parts of the organism. Exemplary hormones comprise endocrine hormones, which are released directly into the bloodstream, and exocrine hormones (or ectohormones), which are secreted directly into a duct, and, from the duct, they flow either into the bloodstream or from cell to cell by diffusion in a process known as paracrine signaling. Hormones are produced by various multicellular organisms and in particular vertebrates. In particular, vertebrate hormones can be categorized in three chemical classes: Peptide hormones, Lipid and phospholipid-derived hormones and Monoamines. Peptide hormones consist of chains of amino acids. Examples of peptide hormones include insulin and growth hormone. Lipid and phospholipid-derived hormones derive from lipids such as linoleic acid and arachidonic acid and phospholipids. The main classes are the steroid hormones that derive from cholesterol and the eicosanoids. Examples of steroid hormones are testosterone and cortisol. Monoamines derived from aromatic such as phenylalanine, tyrosine, and tryptophan by the action of aromatic amino acid decarboxylase enzymes. Examples of monoamines are thyroxine and adrenaline. For the purposes of the present application, hormones will be peptides, lipid and phospholipid-derived hormones and monoamines that are released from endocrine cells of the gastrointestinal tract including the pancreas.

The term "metabolic hormone" as used herein indicates hormones that are released by the endocrine system to regulate the metabolism networks of cells and organs in an individual. In particular, metabolic hormones can be peptide based hormones that affect and regulate the metabolism networks of cells and/or organs in an individual. Exemplary metabolic hormones comprise cholecystokinin (CCK), glucagon like peptide-1 (GLP-1) and peptide Tyrosine Tyrosine (PYY).

In an embodiment, modulating release of a metabolic hormone and a related biological process thereof in an individual can be performed by administering to the individual an effective amount of one or more ligands capable of affecting conformational change of one or more target GI bitter taste receptor in the individual.

The term "bitter taste receptor" or "bitter tastant receptor" indicates the family of mammalian taste receptors that detect the sensation of bitterness, and comprise a distinct subfamily of G protein-coupled receptors (GPCRs) that doesn't share any homology to other GPCRs. In particular, human bitter taste receptor family (TAS2Rs) comprises of ~25 bitter taste receptors. Being GPCRs these receptors exhibit multiple conformations each associated with different biological response, such as upregulation or downregulation of one or more intracellular pathways. Identification of the conformation can be performed with methods and techniques such as the methods described in Examples 1 to 3 of the present paper as well as other methods and techniques identifiable by a skilled person. Detection of TAS2R in active or inactive conformations can be performed with methods identifiable by a skilled person which comprise methods in silico as well detection of biological response that is known to be associated with either one of the active or inactive conformations. For example detection of bitter tastants receptors' activation can be performed by measurement of gustducin, and/or transducin which are released from an heterotrimeric G protein following conversion of the TAS2R into active conformation [Wong 1995].

Another exemplary biological response that is associated with the conversion or maintenance of TAS2R into an active conformation is provided by increase in intracellular $Ca^{2+}$ concentration which typically with TAS2R receptor in an active conformation in the cell where the $Ca^{2+}$ is detected. Detection of gustducin/transducin can be performed by imunnostaining the cell with antibodies for gustducin/transducin or by detection of any of the biological processes associated therewith. Detecting changes in intracellular $Ca^{2+}$ concentration can be performed by standard assays for GPCRs and intracellular $Ca^{2+}$ measurements [Tsien 2003; Zacharias 2000; Zhang 2002]. Additional biological responses associated with TAS2R in an active conformation comprise: i) activation of a phosphodiesterase [Keravis 2010]; ii) alteration of potassium ion channel activity [Scanziani 2009; Schultz 1998]; iii) cell electrical changes [Scanziani 2009]; iv) hormone or neurotransmitter release, and/or additional responses as will be understood by a skilled person upon reading of the present disclosure.

The term "GI bitter taste receptor" or "GI bitter tastant receptor" as used herein indicates bitter taste receptors located in a gastrointestinal tract (GI tract) of an individual. A gastrointestinal tract can comprise the entire gastrointestinal tract of the individual as well as any portion thereof, such as stomach, small intestine, duodenum, jejunum, ileum, large intestine, separately or in any combination. Typically, the GI bitter taste receptors are located on the luminal facing surface of endocrine cells placed in the epithelium of GI tract; and in the islets of Langerhans of the pancreas. Different subset of bitter taste receptors are expected to be located into different types of GI cells. An exemplary list of GI cells known or expected to present bitter tastants receptors is shown in Example 13. In particular, a type of GI cells is known or expected to provide a biological response associated to conformations (such as one or more of the active conformations as well as the inactive conformation) of specific TS2Rs which is determined by the specific type of cell.

The term "ligand" as used herein indicates is a molecule that is recognized by a particular receptor and binds the receptor in one or more binding sites. Examples of ligands include, but are not restricted to, agonists and antagonists for cell membrane receptors, toxins and venoms, viral epitopes, hormones, hormone receptors peptides, enzymes, enzyme substrates, co factors, drugs (e.g. opiates, steroids, etc.), lectins, sugars, polynucleotides, nucleic acids, oligosaccharides, proteins, and monoclonal antibodies. Formation of a "ligand receptor pair" as used herein indicates combination of the ligand and receptor molecules through molecular recognition to form a complex, which can be detected by a variety of ligand receptor binding assays known to a skilled person [Lefkowitz 1970; de Jong 2005]. Typically, in a ligand two portions can be identified: a first portion that is active with respect to the binding of the ligand to a corresponding receptor and a second portion that is passive with respect to said binding and corresponding formation of a ligand receptor pair. In particular, a skilled person will understand and will be able to identify an active portion of a ligand that is involved in the binding and interact or cause interaction with a corresponding binding site of the receptor and a passive portion that is instead not involved and does not affect said binding and formation of a corresponding ligand receptor pair.

In some embodiments herein described, formation of a ligand receptor pair affects the conformation of the bitter taste receptor and in particular either retains an existing conformation or converts the existing conformation into a new conformation. For example, in some of those embodiments the ligand is an antagonist of the receptor and the formation of the ligand pair receptor complex results into retaining of the inactive conformation. In other embodiments the ligand is an agonist of the receptor and formation of the ligand pair receptor complex results in conversion of the inactive form into one or more of the active forms of the receptor. TS2R receptor forms are associated in turn with activation or inactivation of at least one intracellular pathway resulting in one or more detectable chemical or biological response.

In several embodiments, at least one of the active conformations of a bitter tastant receptor results in modulation of release of metabolic hormones by endocrine cells where a target receptor is located. In particular, bitter taste receptor ligands (BTRL) can either cause activation of any of the multiple intracellular pathways or prevent activation of any of those intracellular pathways which results in a corresponding modification of the hormone release.

Detection of modulation of a bitter taste GPCR along with its effect on release of a specific hormone or neurotransmitter of interest can be performed by a skilled person in vitro or in vivo by measuring displacement of the hormone or neurotransmitter of interest from its intracellular site to outside the cell in the case of in vitro measurements or into the blood in the case of in vivo measurements or by detection of another biological response as herein described.

Detection of release of a specific hormone can be also performed by detecting release of hormone in extracellular environment and bodily fluids and in particular in blood using techniques identifiable by a skilled person. For example, detection in blood can be performed by separating a sample blood of an individual into plasma, serum and blood cell fractions. Using standard radio-immunoassay (RIA) or enzyme-linked immunosorbent assay (ELISA) techniques, a specific hormone is measured in either the serum or plasma fraction. Typically, both RIA and ELISA require specific antibodies for each hormone to be measured. Suitable antibodies are available for each hormone from commercial sources and academic centers.

In some embodiments activation or inactivation of intracellular pathway can be specifically associated with bitter sensation as will be understood by a skilled person. In those embodiments. In those embodiments the ligand able to affect the conformation of the bitter taste receptor typically comprises one or more bitter tastants. The term "bitter tastant" as used herein indicates a substance that is recognized by bitter taste receptors to elicit sensation of bitterness. Sensation of bitterness can be detected using a reference compound such as quinone. Accordingly, the threshold for stimulation of bitter taste by quinine averages 0.000008 M. The taste thresholds of other bitter substances are rated relative to quinine. Exemplary bitter tastants according to the current disclosure include but are not limited to 6-n-Propylthiouracil (PTU), Phenylthiocarbamide (PTC), Denatonium benzoate and some derivatives thereof. Chemical structures of PTC and PTU (also called PROP) are shown below

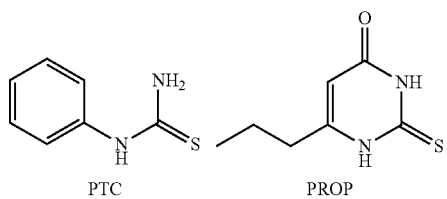

PTC           PROP

In other embodiments, binding of a ligand and related active or inactive conformation of the TAS2R receptor does not involve activation or inactivation of one or more cellular pathways associated with the bitter taste sensation.

In some embodiment the ligand can be a derivative of an existing ligand. The term "derivative" as used herein with reference to a first compound (e.g. PTU), indicates a second compound that is structurally related to the first compound and is derivable from the first compound by a modification that introduces a feature that is not present in the first compound while retaining functional properties of the first compound. Accordingly, a derivative compound of PTU, usually differs from the original compound by modification of the chemical formula that might or might not be associated with an additional function not present in the original compound. A derivative compound of PTU retains however one or more functional activities that are herein described in connection with compound in association with the ability of PTU to bind bitter tastant receptors. Accordingly, derivatives of a PTU or other BTRL comprise any chemically modified form of the tastant, given that the derivatives retain the ability of binding TAS2R38 converting the corresponding taste receptor into one or more active conformations. Derivatives of a PTU or other BTRL also comprise any chemically modified form that retain the ability to bind TAS2R38 but does not retain the ability to modify the inactive conformation of TAS2R38. In embodiments, where the derivatives maintain the ability to affect the conformation of the target receptor, chemical modifications can be performed in the passive portion of the ligand. In embodiments where the derivatives do not retain the ability to modify the inactive conformation of TAS2R38, chemical modifications can be performed on the active as well as passive portion of the ligand. Specific residues to be modified to derive antagonist can be identified by modeling the specific receptor to identify ligands capable of binding TAS2R38. Test the biological response of the ligand to identify the inability of the ligand to activate the TAS2R38 receptor and select the antagonist of TAS2R38. Performing a cavity analysis of the antagonist binding site to identify the PTU-based derivative binding residues that are associated with the antagonistic activity on TAS2R38. A skilled person will be able to identify further antagonist derivatives of PTU by modifying PTU to preserve the same binding site of the PTU-based derivative antagonist. Chemical modifications are determined based on the modeling of tastant binding site in the bitter receptor (e.g. replacing functional group on the ligand to create an additional interaction.). Exemplary chemical modifications of a tastant according to the current disclosure that do not affect the ability to activate conformation of the TAS2R38 include modifying the propyl chain in the PTU (PROP) molecule as this group does not interact with the bitter receptor based on the predicted binding site. Accordingly, in various cases, based on the tastant's predicted binding site, a core structure for an agonist derivative can be defined as the part that interacts with the bitter receptor and hence shouldn't be modified. This will vary for each different ligand. The nature and function of derivatives is discussed later.

An effective amount is the amount that results in a concentration of a ligand at a cellular level that allows formation of a receptor binding complex and hormone release. In some embodiments, for example, an effective amount comprises a concentration of active agents from about 1 micromolar to about 1.25 millimolar. Additional amounts known or expected to be effective for PTC, PTU, Denatonium Benzoate and other ligands herein described comprise from about 0.5 uM to about 1 uM, from about 1 uM to about 2.5 uM, from about 2.5 uM to about 5 uM, from about 5 uM to about 10 uM, from about 10 uM to about 100 uM, from about 100 uM to about 500 uM, from about 500 uM to about 1000 uM, from about 1 mM to about 1.25 mM, from about 1.25 mM to about 2.5 mM, from about 2.5 mM to about 5 mM, from about 5 mM to about 10 mM. Additional effective amounts known or expected to be effective comprise from about 1-2.5 uM, from about 2.6 uM to about 10 uM, from about 11 uM to about 100 uM; from about 101 uM to about 1000 uM; from about 1.25 mM to about 10 mM.

In particular an effective amount in several embodiments is known or expected to be about 2.5 uM. The effective amounts are known or expected for the various ligands herein described alone or in combination and in particular for PTC, PTU, Denatonium Benzoate, Coptisine chloride, Allyl sulfide, Rottlerin, Curcumin, Ellagic acid, Embelin and all the other ligands mentioned in the examples.

In various embodiments, the administering of GI bitter taste receptor ligands, in particular bitter tastant, and related agents can be performed through any route of administration that ensures direct delivery to the desired GI tract. e.g. through oral administration route or other administration route. In particular in some embodiments, the agent is delivered to the lumen of the GI tract and is configured to minimizes systemic transfer of agent in whole or in part from the lumen across the epithelium of the GI tract and enter the blood. In some of those embodiments, minimization of the systemic transfer from the lumen of the GI tract provides action specificity and decreases adverse effects.

In an embodiment, GI bitter taste receptor ligands, related agents and compositions comprising the same, can be delivered into the GI or intestine. In particular, in various embodiments GI refers to the whole GI system, The GI tract in the sense of the present disclosure can include all parts of the GI system from the mouth to the anus; and the attached pancreas and liver. Effects of hormones released from the GI system will or are expected in turn to have secondary effects on pancreas and liver that are desirable for the full beneficial response.

In particular, in some embodiments GI bitter taste receptors are located in GI tract portions upstream of the stomach. The term "upstream" as used herein indicates the portion the mouth of the esophagus. In some embodiments, bitter taste receptors are located in the stomach i.e. any type of bitter taste receptors that are located in the stomach. In some embodiments, bitter taste receptors are intestinal bitter taste receptors i.e. any type of bitter taste receptors that are located in the intestine (both large and small). A distribution of different bitter taste receptors in the GI system is expected. The localization of these receptors in the GI system would affect the choice of the agent being administered as would be understood by a skilled person upon reading of the present disclosure. In particular, the TAS2R and the cells presenting the TAS2R to be targeted can be selected based on the specific hormone to be modulated and the modulation effect desired. Location of the selected cell on the GI tract can be identified. A ligand capable to obtain the desired modulation effect in the selected cell can therefore be administered in the GI tract where the selected cells are located in a suitable amount and form that ensure delivery in the selected tract. For example, increase of GLP-1 can be performed by activating TAS2R38 in cells located in the small and large intestine. A ligand suitable to activate the TAS2R38 in the L cells is PTU. A skilled person would understand that an effective amount of PTU can be delivered directly to the intestine to obtain the desired increase in GLP-1 production release from the L cell into the blood A skilled person will also understand that due to the chemical nature of PTU and the relevant ability to be systemically absorbed by the GI epithelium, PTU can be desirably conjugated with a complementary molecule to minimize absorption and maximize half-life in the intestine.

In an embodiment, the GI and intestinal bitter taste receptors comprise bitter taste receptors located on endocrine cells located on the luminal surface of the GI tract, such as TAS2R38 and TAS2R47. In some of those embodiments, activation of the GI bitter taste receptors results in the release, and consequent systemic distribution, of metabolic hormones from hormone releasing cells, including release from or mediated by said endocrine cells (which cells may be activated from within the GI tract or intestine to release hormones into the blood). Delivery of bitter tastants receptor ligands, combinations and compositions thereof to the GI tract or intestine is also expected to affect said release through intervening, complementary, and alternative steps and processes.

In some embodiments, the method comprises administering to the individual one or more GI bitter taste receptor ligands and/or related agents capable of activating one or more target GI bitter taste receptor in the individual in an effective amount to modulate release of one or more metabolic hormones in the individual.

In an embodiment, GI bitter taste receptor ligands, and agents herein described can be delivered to the GI tract to modulate the release of metabolic hormones from endocrine cells of the GI tract, such as the CCK-containing I-cells and the GLP-1 and PYY-containing L cells. In another embodiment, ligands and agents herein described are expected to be effective on bitter taste receptor present on neural endings of the GI tract and to modulate nerve response which in turn modulates hormone release from endocrine cell in the GI tract.

In an embodiment, GI bitter taste receptor ligands, related agents, compositions, methods and systems are suitable to modulate GLP-1. In some of these embodiments, the ligand can be PTC, PTU, Glycyrrhizic acid ammonium salt, Epigallocatechin gallate, Hyperforin, Berberine chloride, Coptisine Chloride Allyl methyl sulfide, Rottlerin, Curcumin, Ellagic acid, Embelin and/or an agonist derivative thereof. In particular, PTC and PTU, or any of the other ligand applied alone or in combination to the luminal surface of hormone releasing GLP-1 and PYY-containing L cell will result in activation of the TAS2R38 receptor on the luminal surface of the L-cell resulting in the release of hormones GLP-1 and PYY from the hormone containing cells into the blood. In particular, the bitter taste receptor ligands, related agents and combinations thereof can be applied to the luminal surface of the GI tract at concentrations ranges from about 1 uM to about 2.5 uM, from about 2.6 uM to about 10 uM, from about 11 uM to about 100 uM; from about 101 uM to about 1000 uM; from about 1.25 mM to about 10 mM, with particular reference to systems that allow delivery to the specific site of location of the TAS2R38 receptor on GLP-1 and PYY-containing L cells in the GI tract. Other ligands capable to activate TAS2R38 receptors applied to the luminal surface of the GI tract at concentrations from about 1 uM to about 2.5 uM, from about 2.6 uM to about 10 uM, from about 11 uM to about 100 uM; from about 101 uM to about 1000 uM; from about 1.25 mM to about 10 mM, with particular reference to systems that allow delivery to the specific site of location of the TAS2R38 receptor on GLP-1 and PYY-containing L cells in the GI tract are also expected to result in release of GLP-1 and PYY from the hormone containing cells into the blood In an embodiment, GI bitter taste receptor ligands, related agents, compositions, methods and systems are suitable to modulate release of CCK into the blood. In some of these embodiments, the ligand is denatonium benzoate or an agonist derivative thereof. These agents applied alone or in combination to the luminal surface of hormone releasing CCK-containing I cell will result in activation of TAS2R47 receptor located on the luminal surface of the I cell resulting in the release of hormone CCK from the hormone containing cells into the blood. In the particular in some embodiments, the agents are applied to the luminal surface of the GI tract at concentrations from about 1-2.5 uM, from about 2.6 uM to about 10 uM, from about 11 uM to about 100 uM; from about 101 uM to about 1000 uM, from about 1.25 mM to about 10 mM in systems that allow delivery to the specific site of location of the TAS2R47 receptor on CCK-containing I cells in the GI tract. Other ligands capable of activating TAS2R47 receptors applied to the luminal surface of the GI tract at concentrations from about 1 uM to about 2.5 uM, from about 2.6 uM to about 10 uM, from about 11 uM to about 100 uM; from about 101 uM to about 1000 uM; from about 1.25 mM to about 10 mM, with particular reference to systems that allow delivery to the specific site of location of the TAS2R47 receptor on CCK-containing I cells in the GI tract will also result in the release of CCK from the hormone containing cells into the blood.

In an embodiment, GI bitter taste receptor ligands compositions, methods and systems are suitable to modulate PYY. In some of those embodiments, since PYY is expected to be released by L-cells, agents able to modulate GLP-1 are also expected or known to modulate PYY.

In some embodiments, the one or more target GI bitter taste receptor comprises TAS2R38, and the one or more metabolic hormones comprises GLP-1 and PYY. In other embodiments, the one or more target GI bitter taste receptor comprises TAS2R47, and the one or more metabolic hormones comprises CCK.

In some embodiments, the one or more agent comprises a bitter tastant. In particular, in some embodiments, the bitter tastant is selected from the group consisting of PTU, PTC, Denatonium benzoate, a derivative thereof and a combination thereof. In particular, both ligands and agents activating TAS2R47 (e.g. DB) and ligands and agents activating TAS2R38 (e.g. PTU and PTC) can be applied alone or in combination to the luminal surface of the GI tract at concentrations from about 1 uM to about 2.5 uM, from about 2.6 uM to about 10 uM, from about 11 uM to about 100 uM, from about 101 uM to about 1000 uM, from about 1.25 mM to about 10 mM. In some of those embodiments, performed in systems that allow delivery to the specific site of location of the TAS2R47 receptor or TAS2R38, respectively, administration is known or expected to result in the release of hormones into the blood. In some embodiments, ligands and agents that activate TAS2R47, are known or expected to result in release of the hormone CCK from 1 cells in the upper part of the intestine into the blood. In an embodiment, agents or ligands that activate TAS2R38 are known or expected to result in release of the hormones GLP-1 and PYY from the L cell in the lower part of the intestine the blood.

In more particular, in some embodiment, the bitter tastant is selected from the group consisting PTU, PTC, a derivative thereof and a combination thereof, and the one or more metabolic hormones comprises GLP-1 and PYY. In other embodiments, the bitter tastant is selected from the group consisting of Denatonium benzoate, a derivative thereof and a combination thereof, and the one or more metabolic hormones comprises CCK. In some embodiments, the combination can being particular delivered in forms that do not leave the intestinal lumen. In this way, each would be delivered to the proper location in the intestine. In particular, in some of these embodiments, combination can be administered before and during a meal. Because of the kinetics of movement, the ligands for the I cell will reach the I cell before the ligands for the L cell reach the L cell. Accordingly, an effect of CCK that predominantly slow emptying of the stomach is expected to occur initially. For example in one case at about 30 min to about 2 hours after administration of the agents, the ligands for the L cell is expected to reach the target cells and initiate release of GLP-1 and PYY which have effects on gastric emptying like CCK but also promote satiety and insulin release. The combination of effects is expected to be beneficial for both weight control and diabetes as well as the consequences of these disorders. In some embodiments, a sustained benefit is expected with a combination of ligands and/or agents administered before and with all meals for a prolonged amount of time (e.g. for many months).

In some embodiments, the one or more agents comprises a bitter tastant, the one or more target GI bitter taste receptor comprises TAS2R47 located on I cells and TAS2R38 located on L cells, and the one or more hormones comprises CCK, GLP-1 and PYY. In particular, in some embodiments, wherein the one or more agent comprises a bitter tastant, the one or more target GI bitter taste receptor comprises TAS2R38 located on L cells, and the one or more hormones comprises PYY, GLP-1 located in the L cell. In other embodiments, wherein the one or more agent comprises a bitter tastant, the one or more target GI bitter taste receptor comprises TAS2R47 located on I cells, and the one or more hormones comprises CCK located in the I cell. In more particular, in some embodiments, the bitter tastant is selected from the group consisting of PTU, PTC, Denatonium benzoate, a derivative thereof and a combination thereof, the one or more target GI bitter taste receptor comprises TAS2R38 located on L cells, and the one or more hormones comprises PYY, GLP-1. In other embodiments, the bitter tastant is selected from the group consisting of PTU, PTC, Denatonium benzoate, a derivative thereof and a combination thereof, the one or more target GI bitter taste receptor comprises TAS2R47 located on I cells, and the one or more hormones comprises CCK.

In some embodiments, the one or more agent is a composition comprising one or more bitter tastant. In particular, in some embodiments, the one or more bitter tastant is selected from the group consisting of PTU, PTC, a derivative thereof and a combination thereof, and the one or more metabolic hormones comprises GLP-1 and PYY. In other embodiments, the one or more bitter tastant is selected from the group consisting of Denatonium benzoate, a derivative thereof and a combination thereof, and the one or more metabolic hormones comprises CKK.

In some embodiments, the one or more agent comprises a composition comprising one or more bitter tastant. In particular, in some embodiments, the one or more bitter tastant is selected from the group consisting of PTU, PTC, Denatonium benzoate, a derivative thereof and a combination thereof. The one or more target bitter taste receptor comprises TAS2R38 located on L cells, and the one or more hormones comprises PYY, GLP-1. In other embodiments, the one or more bitter tastant is selected from the group consisting of PTU, PTC, Denatonium, a derivative thereof and a combination thereof. The one or more target bitter taste receptor comprises TAS2R47 located on L cells, and the one or more hormones comprises CKK.

In some embodiments, the one or more agent comprises a bitter tastant and the administrating is performed by orally administrating the one or more agent into a GI tract of the individual, the one or more target GI bitter taste receptor comprises TAS2R38 and TAS2R47 and the one or more metabolic hormone comprises PYY, GLP-1 and CCK, wherein the bitter tastant is suitable for oral administration to the GI tract, in particular, neither the bitter tastant nor its metabolites causes adverse effects delivered in a system that minimizes absorption across the GI tract and distribution systemically. In particular, in some embodiments, the one or more target GI bitter taste receptor comprises TAS2R38, and the one or more metabolic hormone comprises PYY, GLP-1. In other embodiments, the one or more target GI bitter taste receptor comprises TAS2R47, and the one or more metabolic hormone comprises CCK.

In some embodiments, the agent comprises bitter tastant capable of transiting to and through part or all of the GI tract or intestine, upon oral or other administration In embodiments, where administration is performed by oral route rectal route or other route that is suitable to deliver the ligand to the desired tract of the intestine, ligands or combination thereof can be in formulation such that the ligand does not lose its functionality through degradation, additive reaction, digestive enzymatic or other process, metabolic or bacterial process, or otherwise, prior to or upon delivery to the portion or portions of the GI tract or intestine wherein reside the bitter taste receptors to which the ligand is intended to be delivered.

In some embodiments, the ligand is capable of transiting to and through part or all of the GI tract or intestine, upon oral or other administration route of administration. In other embodiments, the ligand naturally has a minimal absorption through the GI tract or is modified to minimize absorption across the GI tract. In some embodiments, to prolong the half-life of a ligand in the intestine, the ligand is expected to be non-degrading and in at least some cases to be resistant or impervious to degradation by the digestive enzymes or other chemicals and action of the stomach and intestine. A tether if present is to be connected to the agent in a way and/or at such a point on the agent that it does not interfere with/inhibit the agent's functioning/binding.

In some embodiments, ligands can be comprised in a composition, provided in combination or otherwise modified for use as or in an agent. In particular, in some embodiments, ligands are comprised in compositions that are formulated to minimize absorption of the ligand across the GI tract In some embodiments, a ligand or agent or a combination thereof can be comprised in composition that delivers an agent specifically to the vicinity of a cell or part of the intestine, or directly to a specific cell. In particular, in some embodiments, delivery can be performed by encapsulation (including micelle encapsulation), in other embodiment by conjugation to a chain of multipart block co-polymers that target a cell or environment and then release or activate the agent/ligand 'payload' according to techniques and procedures identifiable by a skilled person In some embodiments, a ligand can be administered in combination with a complementary molecule configured for interfering with systemic absorption of the bitter tastant.

The term "complementary molecule" as used herein indicates a molecule configured to modify distribution of at least one BTRL to minimize absorption through GI tract without substantially altering ability of the ligand to bind a corresponding TAS2R(s). Exemplary types of the complementary molecule according to the current disclosure, include polymers such as nucleic acid, protein, PEGs, monosaccharide and oligosaccharides (such as cellulose) These molecules are known or expected to prevent the absorption of BTRLs in the GI system to prolong their effect on the hormone release. Exemplary complementary molecules comprise monosaccharides, oligosaccharides, amino acids, peptides, and polymers such as cellulose or PEG.

The term "monosaccharide" as used herein indicates the most basic units of biologically important carbohydrates. Typically monosaccharides have the chemical formula $C_x(H_2O)_y$, where x is at least 3. Monosaccharides can be classified by the number x of carbon atoms they contain: diose (2) triose (3) tetrose (4), pentose (5), hexose (6), heptose (7), and so on. Monosaccharides can be classified in linear chain monosaccharide, open chain stereoisomers, and cyclic isomers. Examples of monosaccharides include glucose (dextrose), fructose (levulose), galactose, xylose and ribose. Monosaccharides are the building blocks of disaccharides such as sucrose and polysaccharides (such as cellulose and starch). Further, each carbon atom that supports a hydroxyl group (except for the first and last) is chiral, giving rise to a number of isomeric forms all with the same chemical formula. For instance, galactose and glucose are both aldohexoses, but have different chemical and physical properties.

The term "oligosaccharide" as used herein, indicates a saccharide polymer containing a small number (typically two to ten) of component sugars, also known as simple sugars (monosaccharides). Oligosaccharides can have many functions; for example, they are commonly found on the plasma membrane of animal cells where they can play a role in cell-cell recognition. In general, they are found either O- or N-linked to compatible amino acid side-chains in proteins or to lipid moieties (see glycans).

As used herein the term "amino acid", "amino acidic monomer", or "amino acid residue" refers to any of the twenty naturally occurring amino acids, non-natural amino acids, and artificial amino acids and includes both D an L optical isomers. In particular, non-natural amino acids include D-stereoisomers of naturally occurring amino acids (these including useful ligand building blocks because they are not susceptible to enzymatic degradation). The term "artificial amino acids" indicate molecules that can be readily coupled together using standard amino acid coupling chemistry, but with molecular structures that do not resemble the naturally occurring amino acids. The term "amino acid analog" refers to an amino acid in which one or more individual atoms have been replaced, either with a different atom, isotope, or with a different functional group but is otherwise identical to original amino acid from which the analog is derived. All of these amino acids can be synthetically incorporated into a peptide or polypeptide using standard amino acid coupling chemistries. The term "polypeptide" as used herein includes polymers comprising one or more monomer, or building blocks other than an amino acid monomer. The terms monomer, subunit, or building blocks indicate chemical compounds that under appropriate conditions can become chemically bonded to another monomer of the same or different chemical nature to form a polymer. The term "polypeptide" is further intended to comprise a polymer wherein one or more of the building blocks is covalently bound to another by a chemical bond other than amide or peptide bond.

The term cellulose as used herein indicates an organic compound with the formula $(C_6H_{10}O_5)_n$, a polysaccharide consisting of a linear chain of several hundred to over ten thousand β(1→4) linked D-glucose units. Cellulose is the most common organic compound on Earth. About 33% of all plant matter is cellulose (the cellulose content of cotton is 90% and that of wood is 40-50%). Methods and techniques for synthesis and uses of cellulose to be administered in a composition and in particular a pharmaceutical composition for individuals are identifiable by a skilled person.

The term "Polyethylene glycol" or "PEG" as used herein indicates a polyether compound. Exemplary PEG molecules comprise PEG, PEO, or POE which refer to an oligomer or polymer of ethylene oxide. The three names are chemically synonymous, but historically PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol. In some embodiments, PEG suitable to be used as a complementary molecule is PEG 10,000 [Kerckhoffs, 2010].

In an embodiment, the ligand can be comprised in composition together with a complementary molecule configured to minimize absorption of the ligand in the GI system. In an embodiment, a composition can comprise more than one agent and/or ligands as well as suitable vehicle or additives. Exemplary compositions comprise PTU-Cellulose or PTU PEG A skilled person can identify complementary molecule suitable to be not absorbable across GI tract, and linking or encapsulating to meet the criteria.

In some embodiments, the bitter tastant receptor ligand can be conjugated with the complementary molecule. The term "conjugate" or "conjugation" as used herein indicates association of at least two molecules into a complex through covalent binding. The term "covalent binding" as used herein indicates a process of formation of a chemical bonding that is characterized by sharing of pairs of electrons between atoms, known as the covalent bond. Covalent bonding indicates a stable balance of attractive and repulsive forces between atoms when the atoms share their electrons, and includes many kinds of interaction, including σ-bonding, π-bonding, metal to metal bonding, agostic interactions, and three-center two-electron bonds. In several embodiments, the conjugating group is expected to be a reactive group like carboxylic acid and azide shown in FIG. 13, which facilitates the attachment of most types of complementary molecules. In particular, in some embodiments, conjugation can be performed by direct attachment of the bitter taste receptor ligand with the complementary molecule. In some embodiment, the complementary molecule can be conjugated by indirect attachment wherein the bitter taste receptor ligand is covalently bound to the complementary molecule through one or more additional molecule (e.g. a linker enabling or facilitating attachment of the ligand to the complementary molecule). In particular, conjugation is performed so that the bitter taste receptor ligand in the resulting agent comprising the ligand linked to the complementary molecule is presented for binding to a corresponding GI bitter taste receptor.

The term "present" as used herein with reference to a compound or functional group indicates attachment performed to maintain the chemical reactivity of the compound or functional group as attached. Accordingly, a functional group presented on a ligand, is able to perform under the appropriate conditions the one or more chemical reactions that chemically characterize the functional group.

The term "attach" or "attached" as used herein, refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material.

The term "functional group" as used herein indicates specific groups of atoms within a molecular structure that are responsible for the characteristic chemical reactions of that structure. Exemplary functional groups include hydrocarbons, groups containing halogen, groups containing oxygen, groups containing nitrogen and groups containing phosphorus and sulfur all identifiable by a skilled person. In particular, functional groups in the sense of the present disclosure include a carboxylic acid, amine, triarylphosphine, azide, acetylene, sulfonyl azide, thio acid and aldehyde. In particular, for example, the first functional group and the second functional group can be selected to comprise the following binding partners: carboxylic acid group and amine group, azide and acetylene groups, azide and triarylphosphine group, sulfonyl azide and thio acid, and aldehyde and primary amine. Additional functional groups can be identified by a skilled person upon reading of the present disclosure. As used herein, the term "corresponding functional group" refers to a functional group that can react to another functional group. Thus, functional groups that can react with each other can be referred to as corresponding functional groups.

In some embodiments, the conjugated bitter tastant or the composition comprises PTU. In some of those embodiments, PTU is covalently bond to the complementary molecule. In particular, in some embodiments, a single hydrogen atom of PTU as shown in FIG. 11 is replaced by an OH functional group that is shared by, linked to, incorporated in, or incorporated by both PTU and the complementary molecule.

In particular, in some embodiments, the complementary molecule is a nucleic acid. In some embodiments, the complementary molecule is a protein. In some embodiments, the complementary molecule is a monosaccharide. In some embodiments, the complementary molecule is an oligosaccharide.

In some embodiments, the composition comprises PTU and at least two complementary molecules, wherein at least one complementary molecule is covalently bonded to PTU, and at least one other complementary molecule is not covalently bound to the ligand.

Figure 11:
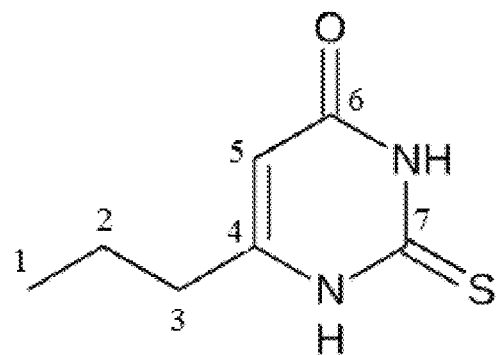
FIG. 11 shows a chemical formula of PTU, an agent according to an embodiment herein described. In the illustration of FIG. 1, the seven carbon atoms are denoted by the numbers 1 through 7. The sulfur, nitrogen and oxygen atoms are denoted S, N, and O, respectively.

In particular, in some embodiments, the covalent bonding between the at least one complementary molecule and PTU is through replacement of a single hydrogen atom of PTU as shown in FIG. 11 by a carboxylic or azide functional group (FIG. 13) that is shared by, linked to, incorporated in, or incorporated by both PTU and the complementary molecule.

In some embodiments, PTU can be modified, composed, encapsulated or otherwise prepared for use in delivery to the GI tract or intestine, or for modulation of GI or intestinal bitter taste receptors and in particular to activate or modulate GI or intestinal bitter taste receptor TAS2R38 or other GI or intestinal bitter taste receptors.

In an embodiment, activating a target bitter tastant receptor in an individual are described. The method comprises administering to the individual an effective amount of one or more agents selected from the group consisting of PTU, PTC, denatonium, a derivative thereof and a combination thereof. The system comprises at least two agents selected from the same group. The composition comprises one or more agent selected from the same group.

In some embodiments, the conjugated bitter tastant agent comprises one or more compound selected from the group consisting berberine chloride, cyanidine chloride, coptisine chloride, any functional derivative thereof and any combination thereof. In some embodiments, the endocrine cells are I-cells. In other embodiments, the endocrine cells are L-cells. In some embodiments, Berberine chloride, cyanidine chloride, coptisine chloride, any functional derivative thereof and any combination thereof can also be provided in methods, compositions and systems herein described as simple ligands. In some of those embodiments, ligands and relate agents can be used in applications for nutraceutical uses.

In an embodiment, use of bitter tastant receptor ligands and related compositions, and to the modulation of GI and intestinal bitter taste receptors, can be directed to modulate the release of GLP-1, PYY, CCK and other metabolic hormones, including, but not limited to, metabolic hormones that modulate Metabolic and Related Diseases and Conditions and biological processes relating to the foregoing. GLP-1, PYY, CCK, and other metabolic hormones are known to be released into the blood by gastrointestinal constituents in the lumen of the GI tract, and are known to regulate functions such as gastric emptying, satiety, insulin secretion, lipid metabolism, and other metabolic-related processes.

The term "condition" as used herein indicates a physical status of the body of an individual (as a whole or as one or more of its parts), that does not conform to a standard physical status associated to a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The wording "associated to" as used herein with reference to two items indicates a relation between the two items such that the occurrence of a first item is accompanied by the occurrence of the second item, which includes but is not limited to a cause-effect relation and sign/symptoms-disease relation.

Accordingly, the term "metabolic condition", "metabolic disease" or "metabolic related condition" as used herein indicates a condition or disease related to one or more metabolic processes and/or dysfunction, including a condition or disease treatable through modulation of release of metabolic hormones. Exemplary metabolic condition or diseases according to the current disclosure include but are not limited to obesity, diabetes, liver diseases and cardiovascular diseases. Because obesity and diabetes are associated with an increased risk of several cancers, treatment of obesity and diabetes will have a beneficial effect on these cancers as well as metabolic syndrome.

The term "biological process" as used herein in the context of biological processes related to a metabolic condition or disease as described above, refers to a biological process that influences and/or causes the metabolic condition or disease as described above, including but not limited to gastric emptying, satiety, insulin secretion, lipid metabolism.

According to several embodiments, bitter taste receptor ligands, and related composition methods and systems are herein described to treat or prevent in an individual a condition associated to a metabolic hormone The term "treatment" as used herein indicates any activity that is part of a medical care for or deals with a condition medically or surgically.

The term "prevention" as used herein indicates any activity, which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "individual" as used herein in the context of administrating a agent includes a single biological organism, including but not limited to, animals and in particular higher animals and in particular vertebrates such as mammals and in particular human beings.

An effective amount and in particular a therapeutically effective amount of a bitter taste receptor ligand or agent alone or in combination comprise from about 1 micromolar to about 1.25 millimolar. Additional amounts known or expected to be effective for PTC, PTU, Denatonium Benzoate and other ligands herein described comprise from about 0.5 uM to about 1 uM, from about 1 uM to about 2.5 uM, from about 2.5 uM to about 5 uM, from about 5 uM to about 10 uM, from about 10 uM to about 100 uM, from about 100 uM to about 500 uM, from about 500 uM to about 1000 uM, from about 1 mM to about 1.25 mM, from about 1.25 mM to about 2.5 mM, from about 2.5 mM to about 5 mM, from about 5 mM to about 10 mM. Additional effective amounts known or expected to be effective comprise from about 1-2.5 uM, from about 2.6 uM to about 10 uM, from about 11 uM to about 100 uM; from about 101 uM to about 1000 uM; from about 1.25 mM to about 10 mM.

In an embodiment, diseases and conditions that can be treated or prevented through release or modulation of release of GLP-1, PYY, CCK or other metabolic hormones include, but are not limited to, obesity; diabetes; other metabolic conditions and diseases; liver diseases and cardiovascular diseases. Because obesity and diabetes are associated with an increased risk of several cancers, treatment of obesity and diabetes is expected to have a beneficial effect on these cancers.

In some embodiments, a bitter taste receptor ligand, and in particular bitter tastants, and/or agent herein described can be comprised in a composition together with a suitable vehicle. The term "vehicle" as used herein indicates any of various media acting usually as solvents, carriers, binders or diluents for the bitter taste receptor ligand comprised in the composition as an active ingredient. Exemplary compositions comprise PTU, PTC, denatonium benzoate, Glycyrrhizic acid ammonium salt, Epigallocatechin gallate, Hyperforin, Berberine chloride, Coptisine Chloride Allyl methyl sulfide, Rottlerin, Curcumin, Ellagic acid, Embelin, a derivative thereof and a combination thereof. In some embodiments, the compositions are formulated for systemic release.

In some embodiments, the ligand or related agents, combination or composition is administered by enteral administration. Enteral administration is a systemic route of administration where the substance is given via the digestive tract, and includes but is not limited to oral administration, administration by gastric feeding tube, administration by duodenal feeding tube, gastrostomy, enteral nutrition, and rectal administration. In particular in several embodiments, the administration suitable for these compounds is an oral one in solid or liquid formulation.

In some embodiments, where the composition is to be administered to an individual the composition can be a pharmaceutical composition, and comprise za bitter taste receptor ligand and a pharmaceutically acceptable vehicle.

In some embodiments, ligand can be included in pharmaceutical compositions together with an excipient or diluent. In particular, in some embodiments, pharmaceutical compositions are disclosed which contain a ligand, in combination with one or more compatible and pharmaceutically acceptable vehicle, and in particular with pharmaceutically acceptable diluents or excipients.

The term "excipient" as used herein indicates an inactive substance used as a carrier for the active ingredients of a medication. Suitable excipients for the pharmaceutical compositions herein disclosed include any substance that enhances the ability of the body of an individual to absorb ligand. Suitable excipients also include any substance that can be used to bulk up formulations with ligand to allow for convenient and accurate dosage. In addition to their use in the single-dosage quantity, excipients can be used in the manufacturing process to aid in the handling of the ligand. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluent include any substance that can decrease the viscosity of a medicinal preparation.

Exemplary compositions for enteral administration include but are not limited to a tablet, a capsule, drops, and suppositories.

In some embodiments, ligands can be administered in combination one with another and/or with other molecules to modulate one or more hormones. There are several types of combinations that are expected to be effective. For example, a combination that results in regulation of both TAS2R38 and TAS2R47 is expected to resulting in release of both CCK and PPY/GLP-1 as will be understood by a skilled person upon reading of the present disclosure. In several embodiments, a combination is expected to have a greater effect than the administration to the single cells. In particular, it is expected that combinations of multiple ligands and in particular bitter tastants can be used to address some conditions associated with hormones and in particular, metabolic hormones. For example, DB and PTU+PEG are expected to be suitable to treat obesity, as their administration is expected to result in the release of both CCK and PYY, each of which addresses satiety. This is expected to occur with other hormones released from other GI-mucosa cells in response to activation by T2R ligands activating a TAS2R receptor on a TAS2R-bearing hormone-secreting cell.

In an embodiment, combination of ligands is expected to provide a beneficial additive effect at an individual endocrine cell type. For example, the cell type can include another type of bitter taste GPCR in addition to TAS2R38 for the L cell or TAS2R47 for the I cell. Examples of other types of taste receptors are expected to include receptors responding to berberine chloride, cyanidine chloride, coptisine chloride.

Suitable schedules of administration that are known or expected to be effective for the method at issue comprise delivery of agents before and during a meal as will be understood by a skilled person upon reading of the present disclosure.

The Examples section of the present disclosure illustrates examples of the compositions and methods herein described as well as the studies carried out by applicants in order to investigate the functional and physical interactions of ligands/agents, combination thereof and bitter taste receptors Further advantages and characteristics of the present disclosure will become more apparent hereinafter from the following detailed disclosure in the Examples given by way or illustration only with reference to an experimental section.

EXAMPLES

The active agents, methods, systems and compositions herein disclosed are further illustrated in the following examples, which are provided by way of illustration and are not intended to be limiting.

Example 1

Methods and Systems to Predict 3D Structures of BTR

The GEnSeMBLE and GenDock methods and systems were used to perform prediction of 3D structure of bitter tastant receptors.

Alignment and Homologize. The sequences of TAS2R38 receptors (SEQ ID NO: 2 to SEQ ID NO: 5) were aligned with the turkey β1 Adrenergic Receptor (thβ1AR) (SEQ ID NO: 1) as shown in FIG. 1. Then the residues of hβ1AR were mutated to the aligned sequences of TAS2R38 receptors and generated the initial 3D structure of TAS2R38 receptors.

Optimization of helices. The predicted TM domains of the protein were extracted to form 7 single helices, which were minimized using the dreiding force field [Mayo 1990] and then merged to form a 7 helix bundles that matches the template.

Construction of a template structure. Given the optimum helices to describe each of the 7 TM domains, they are placed into a 7-helix bundle using the x-ray template. Each experimental template has 42 degrees of freedom: x, y, z, θ, φ and η values for each of the seven TM helices (6×7=42 total). The hydrophobic center is the residue that crosses z=0, which is defined as the plane that runs through the center of the lipid bilayer. It is either calculated from the protein's hydrophobic profile or by homology. The degrees of freedom that were optimized are the tilt angle of the helix θ, the sweep angle of the helix φ, and the rotation of the helix η around the helical axis.

Bihelix. After minimization of helices, all possible 7-helix bundles constructed were considered by allowing each of the 7 helices to take on 12 orientations (30° increments) about their axes, which leads $12^7=35,000,000$ packings of the seven helices of the GPCR. The BiHelix procedure [Goddard 2010] estimates the energies of these 35 million packings using a mean field constructed by considering the 12 sets of nearest neighbor bi-helix interactions, TM1-TM2, TM1-TM7, TM2-TM3, TM2-TM4, TM2-7, TM3-TM4, TM3-TM5, TM3-TM6, TM3-TM7, TM4-TM5, TM5-TM6 and TM6-TM7. Here SCREAM was used to optimize the side-chains for each case [Kam 2008].

CombiHelix. Next, a 7-helix bundle were built into the best 1000 results from BiHelix and re-optimize the side-chains using SCREAM. Each bundle is also immersed in an implicit membrane to compute membrane solvation effects that should disfavor helix rotations that expose charged residues to lipids. This membrane solvation is described in [Goddard 2010].

SuperBiHelix. For the optimum set of rotation angles (η) from step E, now a range of tilts (θ, φ) was sampled simultaneous with η, to obtain the optimum 7-helix bundles. Again the 12 pairs of strongly interacting helices were considered but to account for the effect of tilts. The seven-helix bundle is partitioned into three quadhelix bundles, as shown in FIG. 1. The 2000 structures with the lowest energy for each quadhelix are selected by increasing energy. Finally, from each individual helical conformation list, the best 36 conformations for each helix are used to calculate the energy of $36^7 \approx 8 \times 10^{10}$ full bundles, and output the 1000 combinations estimated from this procedure to have the lowest energies.

SuperComBiHelix. These top 1000 helical bundles from SuperBiHelix are built into 7-helix bundles and the side chains are reoptimized. Then the structure is minimized for 10 steps. This procedure results in an ensemble of low-lying bundles. Examination of the low-lying structures shows which helices are flexible, and may give insight into activation.

Prediction of the extracelluar (EC) and intracelluar (IC) loop structure. To provide initial structures for the three EC and IC loops for use in MD studies of the bitter taste receptors, the alignment of bitter taste receptor with tβ1AR were used to homology threaded these loops to the crystal structure. Then, minimization and dynamics were carried out on the loops with fixed helix bundle atoms. It was expected that these loops to be quite flexible and strongly affected by the solvent, which was treated only implicitly in the previous steps.

Example 2

Methods and Systems to Identify BTR Ligands Binding Sites

The following methods and systems were used to identify of docking ligands and predicted protein structures.

The structures of the BTR with top 10 total energy identified using were chosen from SuperBiHelix step each of which was used to dock agonists PTC and PTU.

The structure and charges of PTC and PTU were calculated using quantum mechanics (B3LYP with the 6-311G** basis set). Two PTC conformers and four PTU conformers were used for docking. The GenDock general procedure for docking was used.

The GenDock method was used to select ligand-binding conformations and calculating their binding energies. The whole protein was partitioned into 32 regions (each with sides of 10 Å) and scanned to find the putative binding regions (with the six hydrophobic residues, I, L, V, F, Y, and W alanized). This ScanBindSite procedure used DOCK4.0 [Kuntz 1982] to generate 1000 conformations in each of these putative regions, selecting the optimum regions based on a combination of burial score and binding energy. These optimum regions were combined and 10,000 poses were generated using DOCK4.0, which were scored using the DREIDING 2 FF [Mayo 1990]. The top 1000 (by energy) were de-alanized, SCREAMed, and then minimized using the DREIDING 3 FF. Then the top 1% (10) was selected for further minimization of the binding site complex (using the unified binding site including all residues within 4 Å of any of the 10 binding poses). The protein and ligand were then neutralized by transferring protons appropriately in salt bridges and protonating or deprotonating exposed side-chains (this leading to more reliable energy comparisons) [Bray 2008]. Then the final docked structure with the best binding energy was selected.

Figure 3:
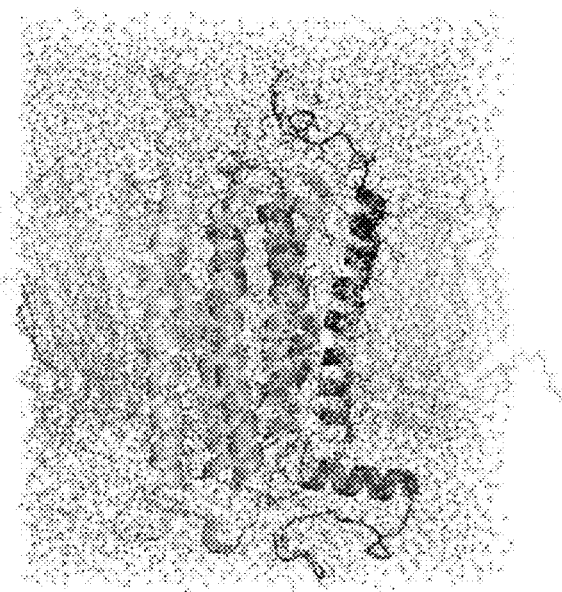
FIG. 3 shows the molecular dynamics simulation box of TAS2R38 bitter receptor with lipid and water. The EC region is at the top.

Molecular Dynamics Simulation. Since the description of lipid and water in BiHelix is implicit with a skimpy layer of lipid bilayer, molecular dynamics (MD) simulations of the predicted structure of bitter taste receptor were performed with and without ligand for 10 ns in explicit lipid bilayer and water. MD simulations using NAMD [Phillips 2005] including explicit water and a periodically infinite lipid were carried out to determine the interactions of the protein with lipid and water. The predicted protein structure was stripped away the lipid molecules, and inserted in a periodic structure of 1-palmytoil-2-oleoylsn-glycero-3-phosphatidylcholine (POPC). In this process, lipid molecules were eliminated within 5 Å of the protein. Then, this was inserted in a box of water molecules and eliminated waters within 5 Å of the lipid and protein. Chloride ions were added to neutralize the charge of the system. The membrane and water molecules were minimized with the protein fixed, and then equilibrated for 500 ps in an NPT simulation. Finally, the entire system was minimized, and then 10 ns of NPT simulation was run. All NPT simulations were run using Langevin dynamics with a damping coefficient of 1 $ps^{-1}$ and a bath temperature of 310 K. The pressure was kept constant by Nose-Hoover Langevin piston pressure control, with a target pressure of 1 atm and barostat oscillation and damping times of 200 fs. The stepsize was 1 fs, with periodic boundary conditions applied. The full system (FIG. 3) contains the predicted protein, 101 lipid molecules, 7528 water molecules, and 19 chlorine ions for a total of 41570 atoms per periodic cell. The box size is 75 Å by 75 Å by 85 Å. The NAMD program was then used to carry out 10 ns of NPT MD with a bath temperature of 310 K.

Example 3

Structure Prediction of hTAS2R38 Bitter Receptor in Humans

Applicants have carried out structure predictions of the human PAV and AVI TAS2R38 receptors. FIG. 21 shows predicted results of the transmembrane (TM) regions having SEQ ID NO: 13 to SEQ ID NO: 26 for this receptor in humans and rats. Applicants used these TM regions to generate optimized helices (TMs 5 (SEQ ID NOs: 21 and 22), 6 (SEQ ID NOs: 23 and 24), and 7 (SEQ ID NOs: 25 and 26) show bends near their Prolines).

In predicting the structure of the PAV and AVI human T2R38 proteins, Applicants found that TM7 of AVI is rotated 30 degrees to that of PAV, such that the bulkier residue, I, is oriented more towards the exterior of the protein. All other TMs display the same rotations. The PAV protein is stabilized by 4 interhelical hydrogen bonds:
a. T32 of TM1 with H68 of TM2 (2.01 Ang.); Q77 of TM2 with Q104 of TM3 (1.85 Ang.);
b. Q77 of TM2 with W108 of TM3 (2.01 Ang.); R138 of TM3 with H126 of TM4 (1.64 Ang.).

The AVI protein is stabilized by 2 interhelical hydrogen bonds:
a. Q77 of TM2 with Q104 of TM3 (1.86 Ang.); Q77 of TM2 with W108 of TM3 (2.02 Ang.)

Preliminary docking simulations of PTC to both PAV and AVI result in PTC binding more strongly to PAV by ~1.6 kcal/mol. PTC forms a 1.84 Ang hydrogen bond with E25 in TM1 of PAV but not in AVI.

Example 4

Modeling the 3D Structure TAS2R38 Bitter Receptor and Comparison of the 3D Structure of Various Polymorphisms of TAS2R38 Bitter Receptors Applicants constructed the structural models of the TAS2R38 bitter receptors (four haplotypes hTAS2R38$_{PAV}$, hTAS2R38$_{AVI}$, hTAS2R38$_{AAI}$ and hTAS2R38$_{PVV}$) using the turkey β1 Adrenergic Receptor (tβ1AR) as a template based on the homology method.

Applicants shortened or lengthened the tβ1AR TMs to fit the TM predictions obtained by homologize technology. After minimization, the initial structures that combine the seven TM segments from tβ1AR (without loops and the eighth helices) are built. The ensemble of a few thousands conformations with different helical rotation angles η, tilt angle θ and sweeping angle φ were generated based on Bihelix and SuperBihelix technology described in [Goddard 2010].

FIG. 1 shows the Transmembranes (TMs) sequence alignments between hTAS2R38$_{PAV}$, hTAS2R38$_{AVI}$, hTAS2R38$_{AAI}$, hTAS2R38$_{PVV}$ and hβ1AR which are used to build the 3D structures by the homology modeling. As shown in Table 1, BiHelix results suggest that the helices of four variants have identical rotational angles except helix 6.

TABLE 1

ComBiHelix results for bitter taste receptors in the β1 adrenergic receptor template.

| Receptor Variants | Rotational Angle | | | | | | | Total Energy (Kcal/mol) |
| --- | --- | --- | --- | --- | --- | --- | --- | --- |
| | H1 | H2 | H3 | H4 | H5 | H6 | H7 | |
| hTAS2R38$_{PAV}$ | 30 | 330 | 60 | 90 | 180 | 270 | 30 | 598.1 |
| hTAS2R38$_{AVI}$ | 30 | 330 | 60 | 90 | 330 | 270 | 30 | 668.9 |
| hTAS2R38$_{AAI}$ | 30 | 330 | 60 | 90 | 240 | 270 | 30 | 584.1 |
| hTAS2R38$_{PVV}$ | 30 | 330 | 60 | 90 | 240 | 270 | 30 | 597.4 |

Figure 4:
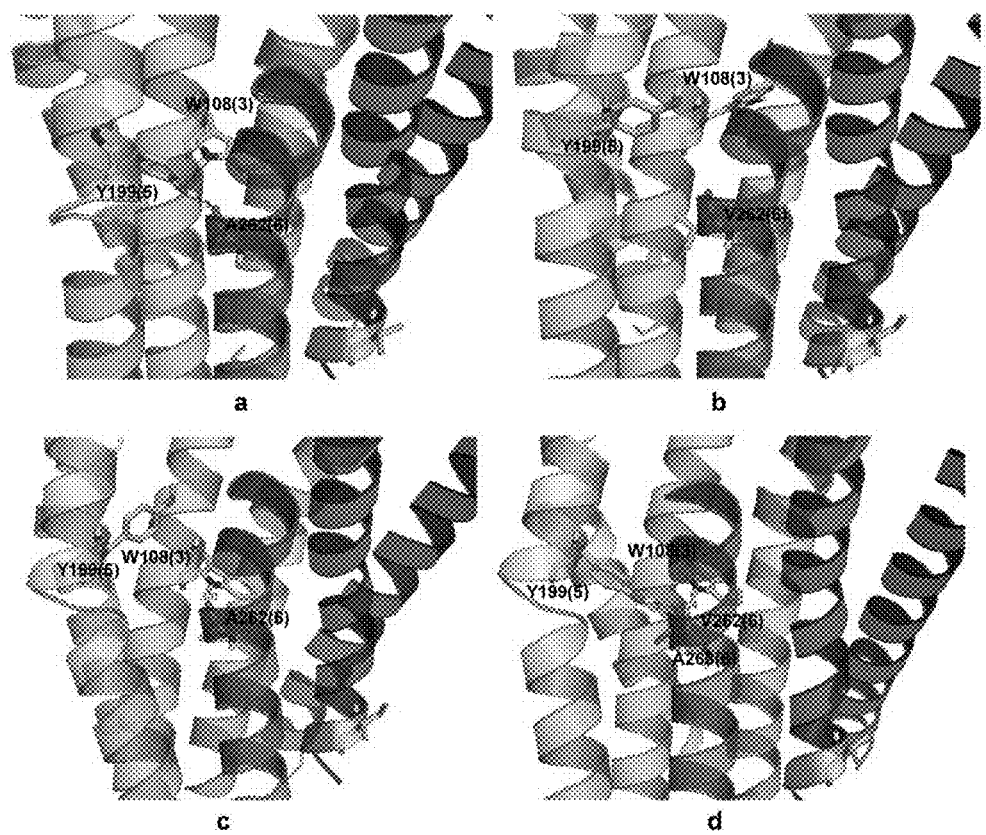
FIG. 4 shows predicted 3D structures of bitter taste receptors hTAS2R38$_{PAV}$ (a), hTAS2R38$_{AVI}$ (b), hTAS2R38$_{AAI}$ (c), hTAS2R38$_{PVV}$ (d) from SuperComBiHelix. (Residues forming interhelical H-bonds are highlighted here)

The TAS2R38 bitter receptors, class C GPCRs, lack some of the well-conserved motifs present in class A GPCRs. Thus it can be expected that the TAS2R38 bitter receptors might have a different set of stabilizing interhelical hydrogen bonds from hβ1AR. The predicted 3D structures of four variants of the TAS2R38 bitter receptors are shown in FIG. 4, and the residues forming interhelical H-bonds are highlighted.

Applicants find the interhelical hydrogen bonds between Y199 (5) and W108 (3), and between Y199 (5) and A262 (6) in hTAS2R38$_{PAV}$ protein. An interhelical bond between W108 (3) and A(V)262 (6) exists in both hTAS2R38$_{AAI}$ and hTAS2R38$_{PVV}$ protein. These interhelical bonds don't exist in the hTAS2R38$_{AVI}$ protein.

To address the 3D structures of these four variants, Applicants performed 10 ns of molecular dynamics simulation on the hTAS2R38$_{PAV}$ and hTAS2R38$_{AVI}$ protein structures.

Figure 5:
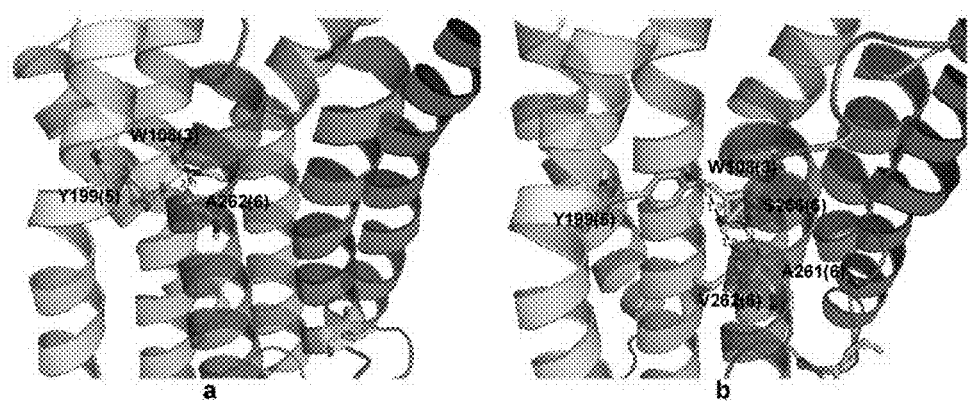
FIG. 5 shows Predicted 3D structures of bitter taste receptors hTAS2R38$_{PAV}$ (a) and hTAS2R38$_{AVI}$ (b) after 10 ns MD with lipid and water. (Residues forming interhelical H-bonds are highlighted here and they are stable during 10 ns MD)
Figure 6:
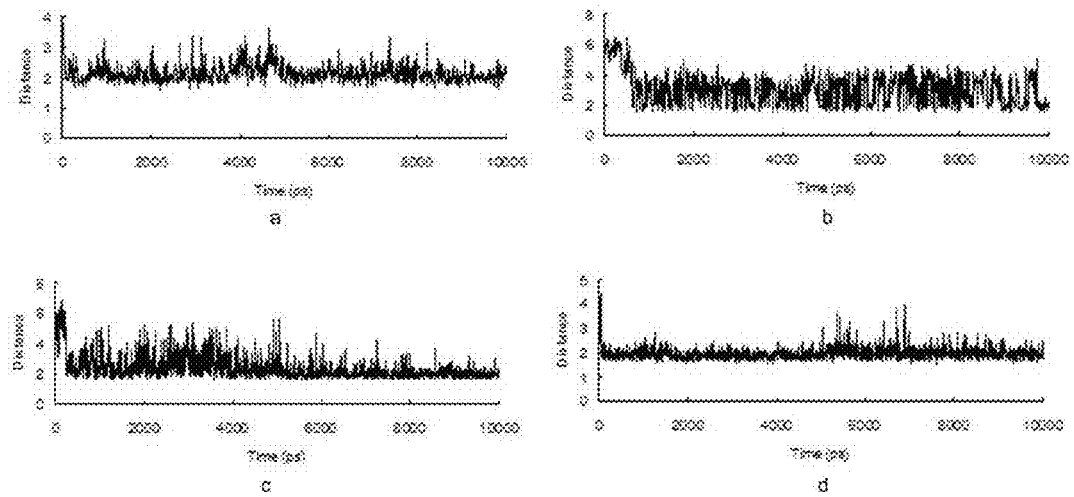
FIG. 6 shows the stability of the predicted hydrogen bonds (HB) in bitter taste receptors over 10 ns MD with full lipid and water. (a) W108-A262 in hTAS2R38$_{PAV}$, (b) Y199-W108 in hTAS2R38$_{PAV}$, (c) Y199-A266 in hTAS2R38$_{AVI}$, (d) W108-A261 in hTAS2R38$_{AVI}$.

FIG. 5 shows the 3D structures of the hTAS2R38$_{PAV}$ and hTAS2R38$_{AVI}$ proteins after 10 ns MD with lipid and water. The hydrogen bonds in hTAS2R38$_{PAV}$ protein were broken, and two new hydrogen bonds between Y199 (5) and W108 (3), and between W108 (3) and A262 (6) which is same to that in hTAS2R38$_{AAI}$ and hTAS2R38$_{PVV}$ protein. We also find 2 new interhelical hydrogen bonds between W108 (3) and A261 (6), and between Y199 (5) and A266 (6) in hTAS2R38$_{AVI}$ protein. FIG. 6 shows that these new H-bonds are all maintained during the 10 ns MD.

Figure 7:
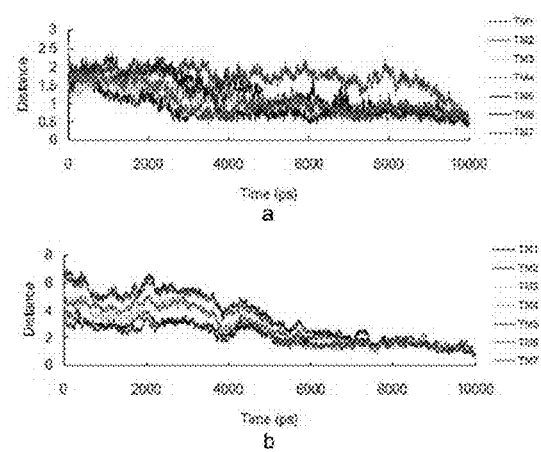
FIG. 7 shows Rmsd evolution of each helix of hTAS2R38$_{PAV}$(a) and hTAS2R38$_{AVI}$(b) during 10 ns MD (the reference is the last frame)

FIG. 7 shows the root mean square deviation (rmsd) time evolution of the helical segments during the 10 ns MD. Here rmsd is with respect to the last frame of the 10 ns trajectory. The total rmsd's range from the initial predicted structure to the final one in the trajectory ranges for 0.5-2.5 Å in hTAS2R38$_{PAV}$ and for 1.0-7.0 Å in hTAS2R38$_{AVI}$. Focusing on the last 2 ns, these fluctuations range from 0.5 to 1.5 Å, except TM2 in hTAS2R38$_{PAV}$ which reaches 2.0 Å.

Example 5

Modeling Binding Sites of TAS2R38 Bitter Receptors for Agonist PTC and PTU

Figures 8C, 8D:
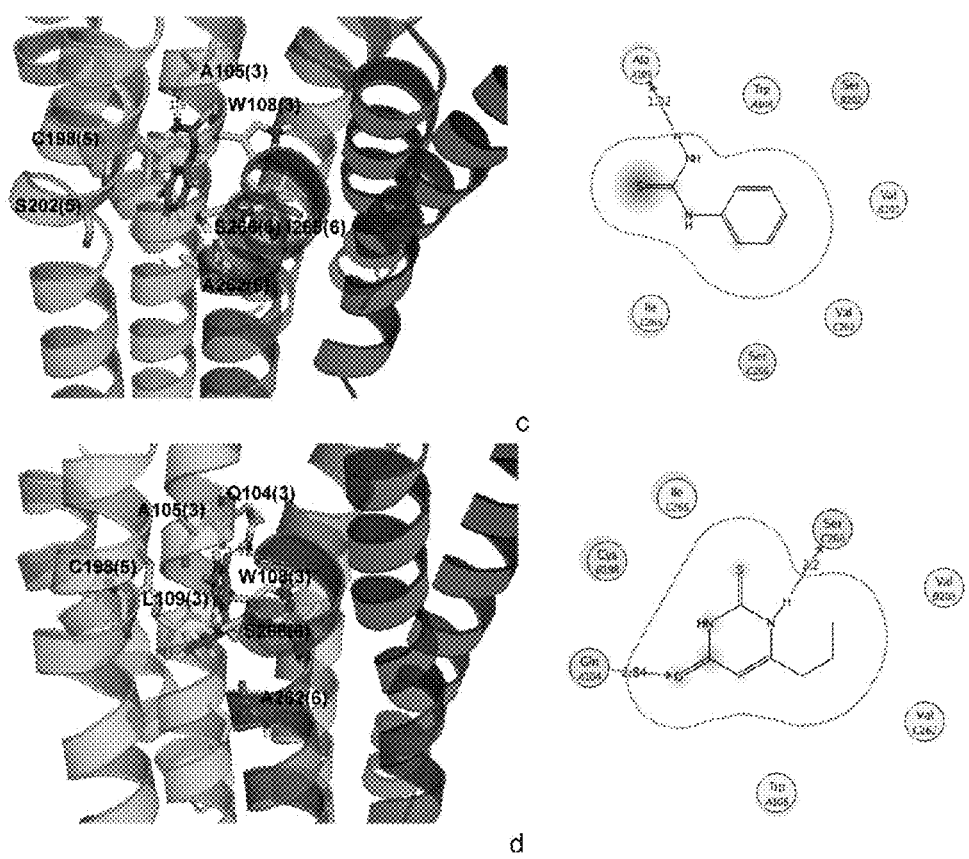
FIG. 8 shows predicted binding sites of agonists in bitter taste receptors. (a) PTC in hTAS2R38$_{PAV}$, (b) PTU in hTAS2R38$_{PAV}$, (c) PTC in hTAS2R38$_{AVI}$, (d) PTU in hTAS2R38$_{AVI}$.

Applicants used the GenDOCK techniques to predict the binding site of agonists to the four predicted (lowest energy) structures of TAS2R38 bitter receptors. The predicted binding sites of agonist PTC and PTU in hTAS2R38$_{PAV}$ and hTAS2R38$_{AVI}$ protein are shown in FIG. 8. PTC and PTU located between the TM 3, 5 and 6 helices. The most important residues (cavity analysis) are (including the interaction energy with ligands in parentheses) stated as follows:
a. Xx hTAS2R38$_{PAV}$ with PTC: ALA262 (−5.336), TYR199 (−5.209), CYS112 (−2.68), TRP108 (−2.579), LEU 109(−2.564), ILE 265(−1.235), PRO204(−1.106), SER 266(−0.976).
b. hTAS2R38$_{PAV}$ with PTU: ALA262 (−4.085), TYR199 (−2.975), TRP108 (−2.127), CYS112 (−1.746), VAL203 (−1.699), LEU109 (−1.655), ALA263 (−1.155), PRO204 (−1.056).
c. −hTAS2R38$_{AVI}$ with PTC: ALA105 (−4.637), TRP108 (−3.035), CYS198 (−2.410), ILE265 (−1.982), LEU109 (−1.937), VAL262 (−1.525), SER202 (−1.289), SER266 (−0.999).
d. hTAS2R38$_{AVI}$ with PTU: SER266 (−4.047), GLN104 (−3.994), CYS198 (−3.075), TRP108 (−3.072), ILE265 (−2.243), VAL262 (−2.032), LEU109 (−1.965), ALA 105 (−1.149).

As shown in FIG. 9, there are two strong hydrogen bonds between PTC and ALA262 in hTAS2R38$_{PAV}$ and the π-π interaction between PTC and TYR199 in hTAS2R38$_{PAV}$. There is a hydrogen bond between PTU and ALA262 in hTAS2R38$_{PAV}$. In hTAS2R38$_{AVI}$, PTC interacts with ALA105 by H-bond, while PTU interacts with SER266 and GLN104 by H-bonds. Furthermore, PTC and PTU were docked to other tasters hTAS2R38$_{AAI}$ and hTAS2R38$_{PVV}$. These results suggest that the residue 262 is very important to taste bitter which agrees with experimental data as reported by [Bufe 2005].

Figures 9A, 9B:
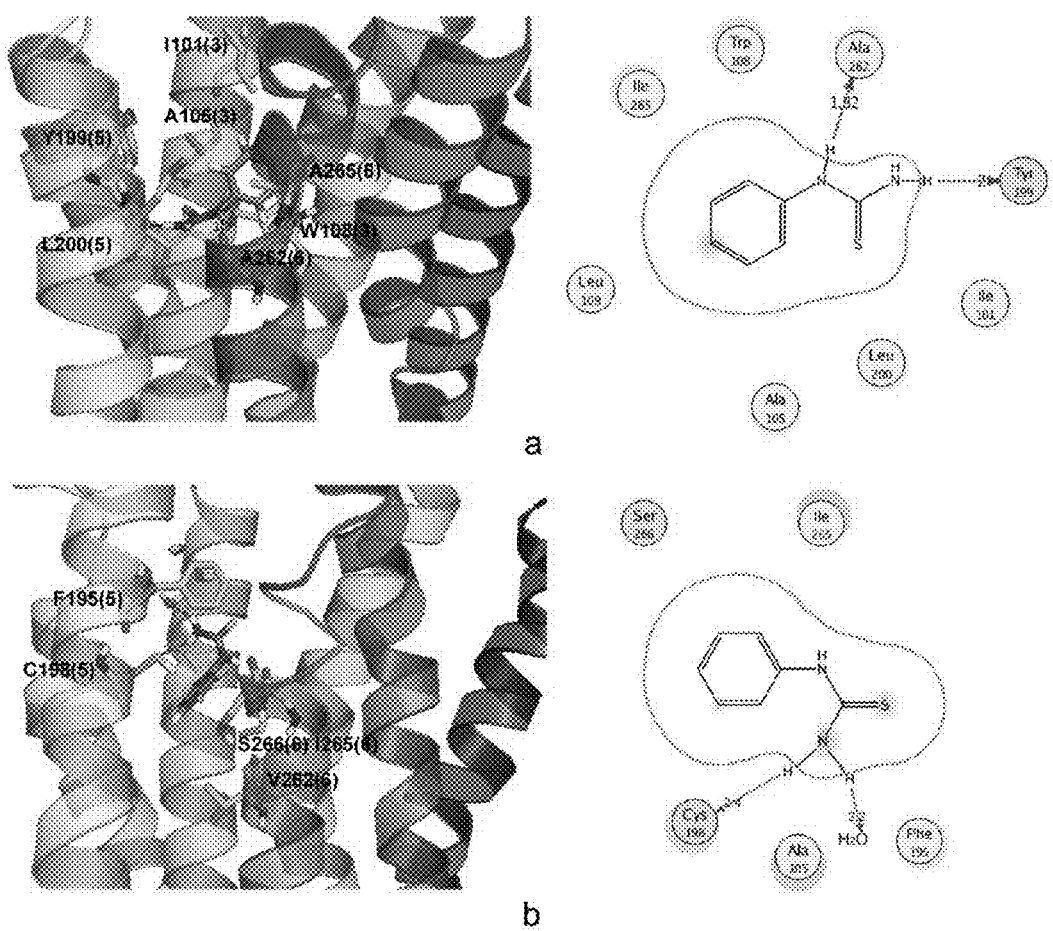
FIG. 9 shows the final binding sites of PTC in hTAS2R38$_{PAV}$(a) and hTAS2R38$_{AVI}$(b) after 10 ns MD with lipid and water. The essential elements of the binding mode are retained but additional favorable interactions are found.
Figure 10:
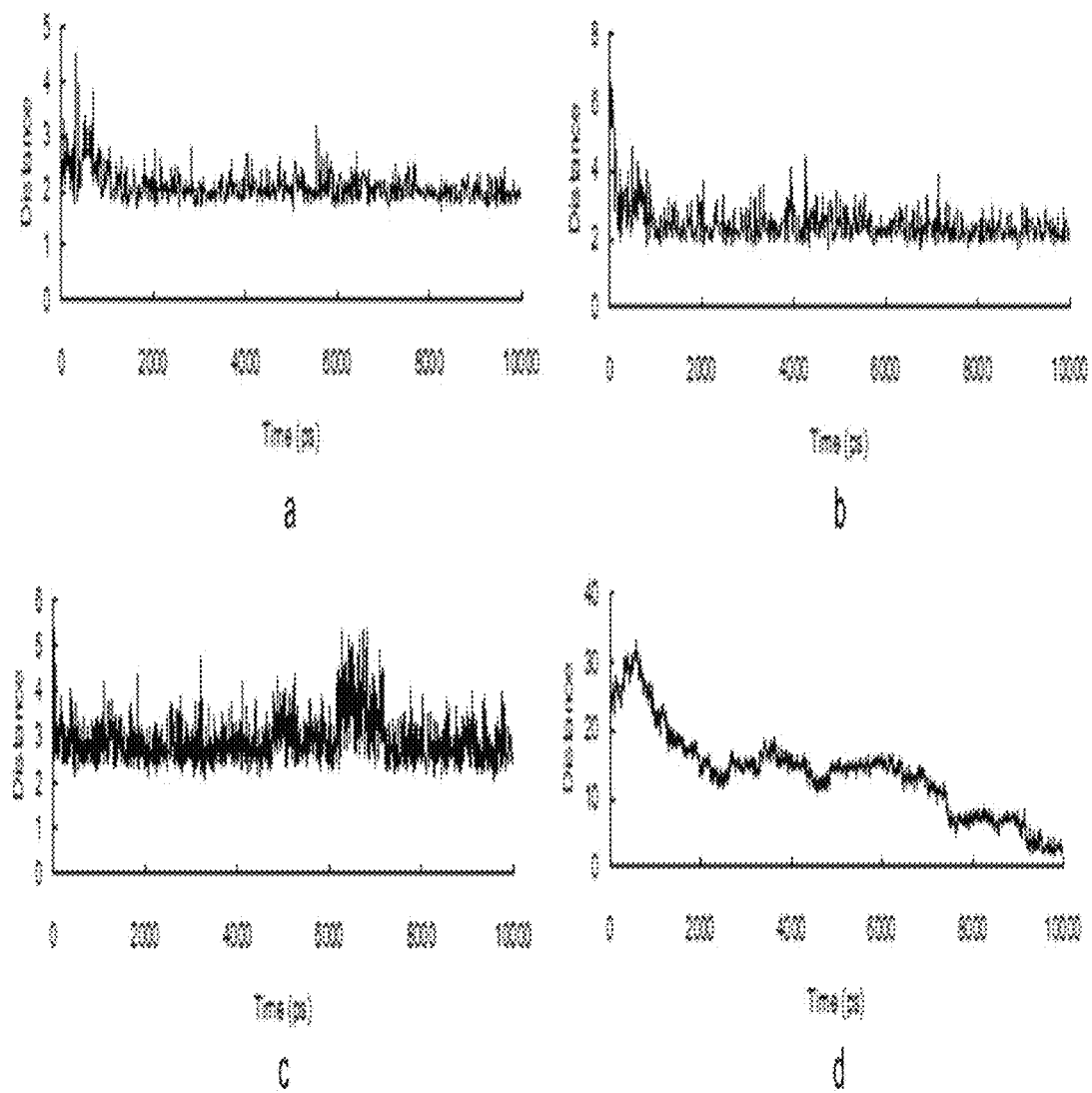
FIG. 10 shows the H-bond distances bonding PTC to hTAS2R38$_{PAV}$ and hTAS2R38$_{AVI}$ during the 10 ns molecular dynamics with lipid and water. (a) PTC-A262 in hTAS2R38$_{PAV}$; (b) PTC-Y199 in hTAS2R38$_{PAV}$; (c) PTC-C198 in hTAS2R38$_{AVI}$; (d) PTC-water in hTAS2R38$_{AVI}$. Note in particular the formation of the last three hydrogen bonds (b, c and d) not present in the original predicted binding site.

After inserting the predicted hTAS2R38$_{PAV}$/PTC and hTAS2R38$_{AVI}$/PTC complexes into the infinite lipid membrane and solvating fully with water (using the procedure described in section 2.3), Applicants performed 10 ns of MD. FIG. 9a compares the structure of the hTAS2R38$_{PAV}$/PTC complex after 10 ns molecular dynamics with the initial predicted structure. Hydrogen bonds of the original predicted structures were found to remain stable during 10 ns dynamics. However, one additional hydrogen bond is formed between —NH$_2$ group of PTC and Y199 (5) in hTAS2R38$_{PAV}$. FIG. 10 shows the time evolution for the hydrogen bonds distances between PTC and hTAS2R38$_{PAV}$.
  i. —NH-A262 (6): the hydrogen bond distance remains mostly between 1.7 and 3.0 Å except the occasional extensions to 4.9 Å during initial 10 ps.
  ii. —NH$_2$-Y199 (5): the initial distance is 6.6 Å, but it quickly contracts to 3.0 Å and then mostly fluctuates between 2.0 Å and 4.0 Å and finally come back to ~2.5 Å.

Thus, Applicants conclude that PTC forms strong interactions with both TM5 and TM6 in the hTAS2R38$_{PAV}$ structure. The binding of ligand between TM5 and TM6 breaks the strong coupling between TM3 and TM6 and between TM3 and TM5.

As shown in FIG. 9b, the ligand in the structure of the hTAS2R38$_{AVI}$/PTC complex after 10 ns molecular dynamics moves up, compared with that of the initial predicted structure. So the initial H-bond between ligand and A105 was broken, and a water molecule moves into the binding site and form H-bonds with the ligand. The insertion of ligand in hTAS2R38$_{AVI}$ protein breaks interhelical hydrogen bonds between W108 (3) and A261 (6), while not that between Y199 (5) and A266 (6).

Example 6

Activation of TAS2R38 Bitter-taste Receptor

The protein structure prediction and MD simulation results indicate that the H-bonds between W108 (3) and A(or V)262 (6) is expected to stabilize the taster hTAS2R38$_{PAV}$, hTAS2R38$_{AAI}$ and hTAS2R38$_{PVV}$, and that the H-bonds between W108 (3) and A261 (6) stabilize the non-taster hTAS2R38$_{AVI}$. Applicants furthermore find that both PTC and PTU can interact with A(or V)262 in taster (hTAS2R38$_{PAV}$, hTAS2R38$_{AAI}$ and hTAS2R38$_{PVV}$) by hydrogen bond, while there is not any H-bond between ligands and non-taster (hTAS2R38$_{AVI}$). Applicants outline here the difference between the agonist-bound taster and agonist-bound non-taster. The major difference involves the position 262 in the bitter taste receptors. The residue 262 is involved in not only the TM3-TM6 interaction but also the binding of agonist to receptors.

Fluorescence experiments on rhodopsin during activation show that TM3-TM6 interaction is involved in GPCR activation [Farrens 1996]. The mutation experiments indicate that position 262 is important to taste bitter for the TAS2R38 bitter receptors [Bufe 2005]. Accordingly, the results indicate that the H-bonds between W108 (3) and A(or V)262 (6) and between agonists and A(or V)262(6) in taster play a crucial role in GPCR activation and bitter-tasting, which is consistent with the experimental data [Bufe 2005].

As shown in Table 1, in addition, the mutation of A262V and V296I results in a larger rotation angle of TM5 in hTAS2R38$_{AVI}$ and make the Y199 closer to TM6 so that the formation of the hydrogen bond between Y199 and A266 could lead to the form of H-bond between W108 and A261 not V262. Although the mutation of A262V exists in the hTAS2R38$_{PVV}$, the smaller rotation angle of TM5 cannot cause the formation of TM5-TM6 hydrogen bond interaction. Thus the hydrogen bond interaction between TM3 and TM6 may pass the signal to intracellular to activate receptor.

Importantly, both PTC and PTU have H-bonds with residue 262 of the tasters (hTAS2R38$_{PAV}$, hTAS2R38$_{AAI}$ and hTAS2R38$_{PVV}$) and not with that of nontaster (hTAS2R38$_{AVI}$). MD simulation results suggest that PTC forms the stable H-bonds with Y199 in TM5 and A262 in TM6 of hTAS2R38$_{PAV}$ structure, while PTC in hTAS2R38$_{AVI}$ prefers to move away from V262. So the residue 262, involved in the interaction between PTC and bitter taster structure, is very important to taste bitter compounds, which agrees with the literature [Bufe 2005].

The 3D structures of four haplotypes of TAS2R38G-protein coupled receptors (GPCRs) were predicted to understand the bitter taste receptors. Applicants find the formation of H-bonds between W108 (3) and A262 (6) in hTAS2R3$_{8PAV}$ (taster) and between W108 (3) and A261 (6) in hTAS2R3$_{8AVI}$ (non-tatser) could stabilize the protein structure. To further validate these structures, Applicants used the GenDock method to predict the binding sites and 3D structures for PTC and PTU bound to hTAS2R3$_{8PAV}$, hTAS2R3$_{8AVI}$, hTAS2R3$_{8AAI}$ and hTAS2R3$_{8PVV}$, respectively. The predicted binding sites position PTC and PTU in the region between TM3, TM5 and TM6. The PTC and PTU could form the H-bonds with residue 262 in the tasters (hTAS2R3$_{8PAV}$, hTAS2R3$_{8AAI}$ and hTAS2R3$_{8PVV}$) and not with that in non-taster (hTAS2R3$_{8AVI}$). The H-bonds between PTC and A262 (6) and between PTC and Y199 in hTAS2R3$_{8PAV}$ are stable. However, PTC in hTAS2R3$_{8AVI}$ moves up away from V262 (6) during 10 ns MD. As a consequence, the results indicate that the hydrogen bond interaction between TM3 and TM6 may pass the signal to intracellular to activate receptor and that the H-bond between agonists and residue 262 in tasters is involved in the bitter tasting, which agrees with the experiment result (Bufe, et al., 2005).

Example 7

Modeling Human TAS2R47 (hTAS2R47) Bitter Taste Receptor

Applicants have obtained a preliminary 3-D structure for hTAS2R47 complexed to a family of ligands tested in a study by [Pronin 2004]. These results are presented below, along with structure prediction results for another GPCR (human prostaglandin DP) that provides validation of the methods.

Applicants used Membstruk to obtain a 3-D structure for hTAS2R47 and used MSCDock to predict the binding sites for four ligands to hTAS2R47: Denatonium (DD), DD2 (Denatonium derivative), 4-Nitro saccharin (4NS), and 6-Nitro saccharin (6NS). These ligands had been used by [Pronin 2004] to study the activation of hTAS2R47, 43, and 44.

Figure 19:
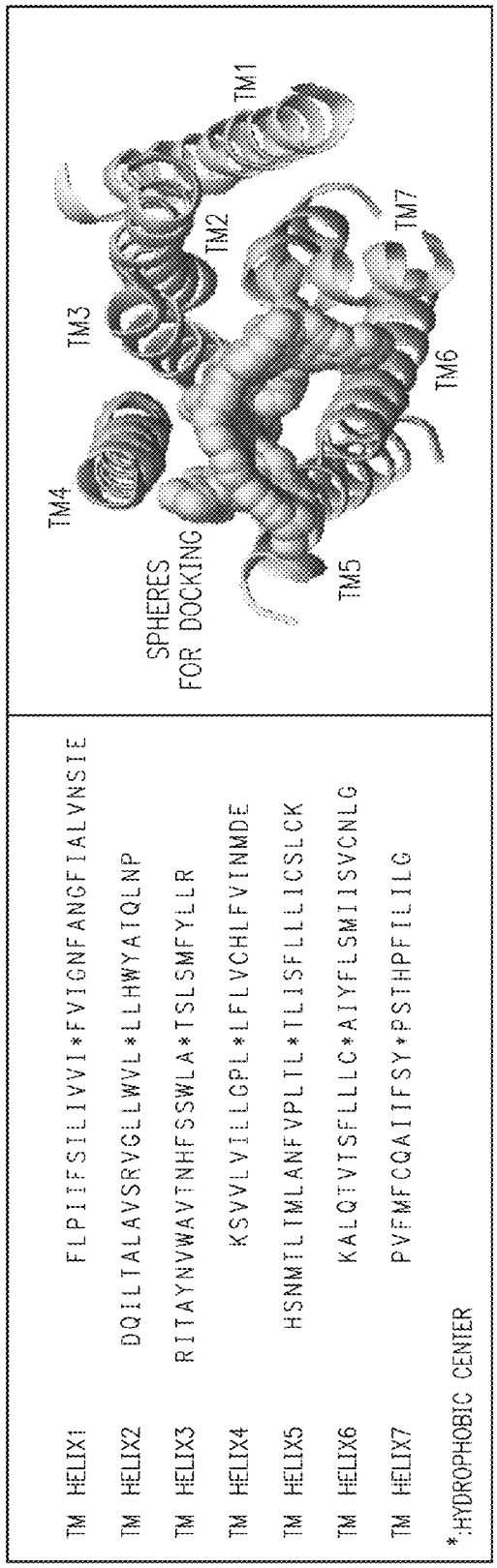
FIG. 19 shows the TM helix predictions for hTAS2R47 including the hydrophobic centers for each helix, which are positioned to lie on a plane passing through the middle of the lipid bilayer (Left panel) and the predicted structure (right panel). The predicted sequences of TM helix 1 to TM helix 7 (SEQ ID NO: 6 to SEQ ID NO: 12) are shown in the left panel.

FIG. 19 shows predicted TM helix domains for hTAS2R47 (SEQ ID NO: 6 to SEQ ID NO: 12) and the predicted TM helix bundle structure along with predicted binding regions used for docking the four ligands. The visible bend in TM7 helix occurs at the position of the middle Proline in TM7 sequence (SEQ ID NO: 12).

Figure 20:
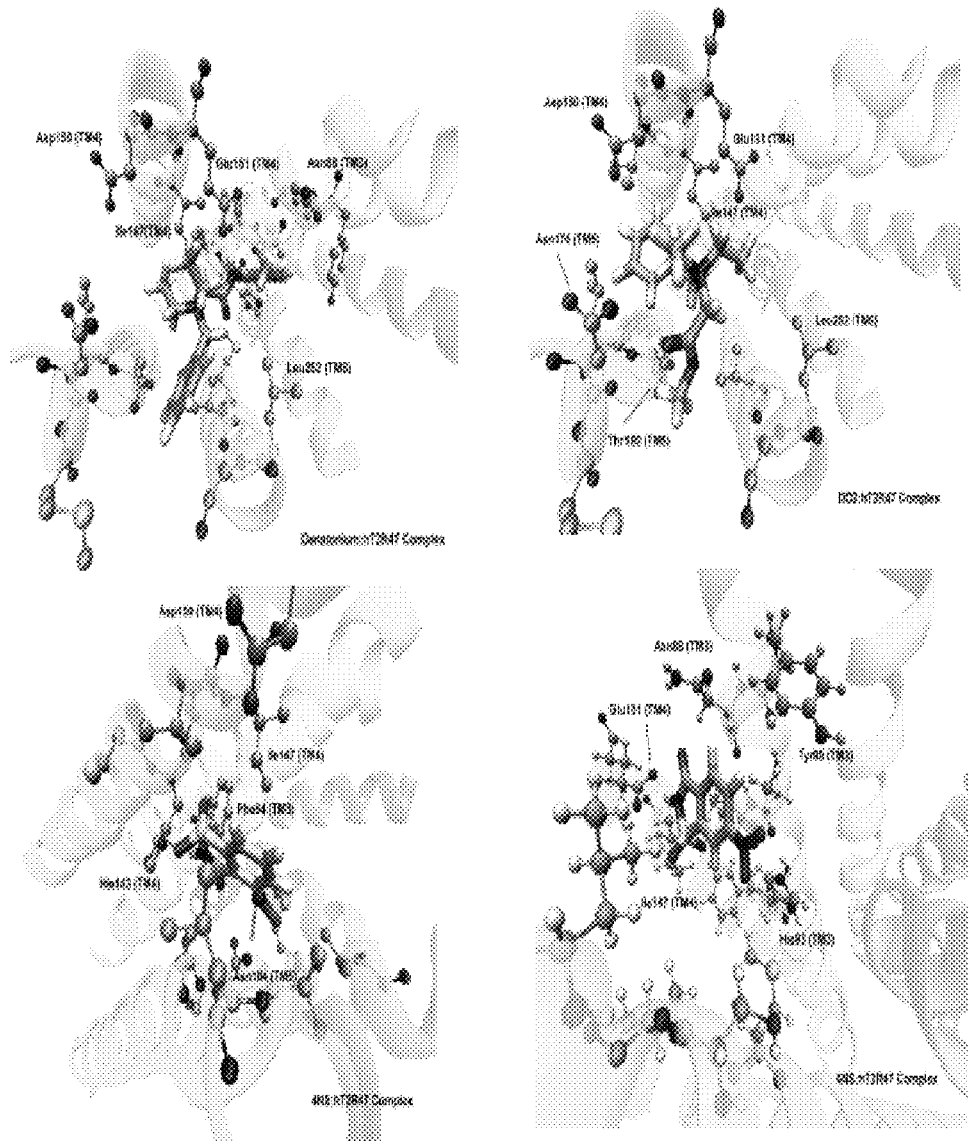
FIG. 20 shows ligand binding sites for Denatonium benzoate, DD2, 4NS, and 6NS complexed to hTAS2R47.

FIG. 20 shows the predicted binding sites for the four ligands. Pronin et al. [Pronin 2004] had observed that hTAS2R47 was activated strongest by Denatonium, whereas DD2 and 6NS activated the receptor to a lesser extent and 4NS acted like a very weak inverse agonist. Applicants find that Denatonium leads to the largest predicted binding energies while the other ligands (DD2, 4NS, 6NS) bind with at least 25% weaker binding energies compared to Denatonium. These results are consistent with those of Pronin et al. [Pronin 2004], assuming that there is a correlation between experimental activation rates and computed binding energies. The predicted interaction of DD with Asp150(TM4) is consistent with mutagenesis studies. The predicted ligand: hTAS2R47 complexes suggest multiple binding sites and multiple binding modes for different ligands.

Example 8

Structure of Prostaglandin DP Receptor and Antagonist Binding Sites

Applicants used the previous generation MembStruk method to predict the structure of the DP prostaglandin receptor and then used this predicted structure with HierDock to predict the binding sites for four families of ligands. This work, summarized below, shows that the predicted GPCR structures are sufficiently accurate for use in drug development.

Figure 22:
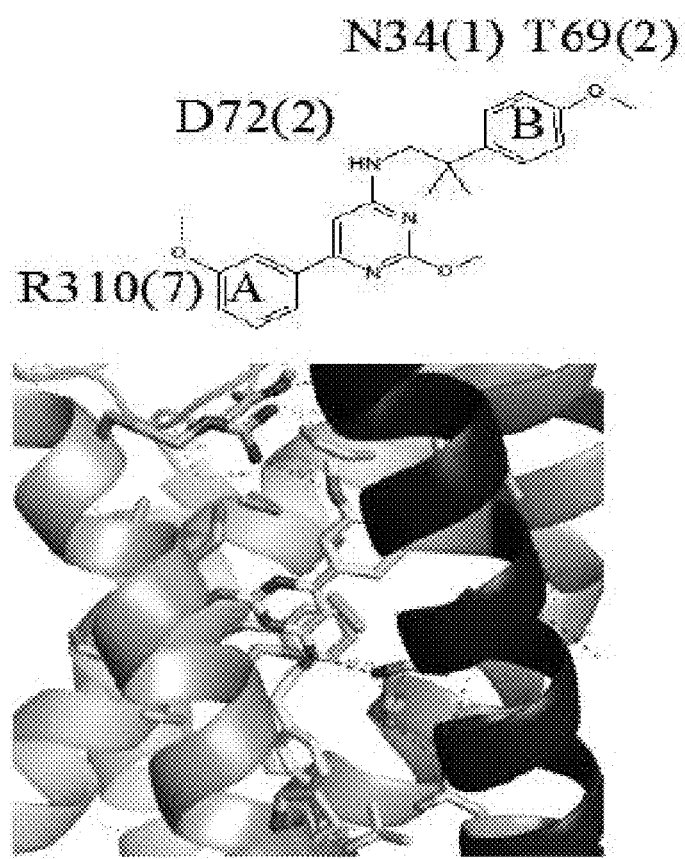
FIG. 22 shows the predicted binding mode for the new pyrimidine antagonist with human DP receptor.

The predicted binding mode of the lead compound is shown in FIG. 22, which provides an explanation of the important interaction of ligand a with the receptor: i) The methoxy on benzene ring A interacts with R310(7), ii) Benzene ring A and pyrimidine ring are located in a hydrophobic cavity that includes L26(1), K76(2), F115(3), S316(7), L312 (7), and 1315(7), iii) The conserved signature residue D72(2) forms a H-bond with the proton of the HN—CH2-C(CH3)2 part of the ligand, iv) Benzene ring B is located among TM127, interacting with N34(1), L68(2), T62(2), and D319 (7). v) O-Methyl on benzene ring B forms an HB with T62(2).

Based on the predicted binding mode, Applicants predicted the binding energies of many modified compounds. Eight of these cases shown in FIG. 23 had been tested experimentally and there was perfect agreement between predicted relative binding energies and relative binding constants [Li 2007].

Compound b has modifications on ring B and the linker HN—CH2-C(CH3)2, leading to better interactions with S316(7) and D319(7), which Applicants predicted would improve the binding energy by 1.4 kcal/mol. Indeed Sanofi-Aventis measured IC50=104 nM for b, an improvement by a factor of 8.

Compounds c and d involve modifications on ring B. Compound d removes a CH2 from the linking, reducing the predicted binding by 1.7 kcal/mol, due to repulsive van der Waals contacts. This was confirmed experimentally, with an increase of IC50 to 1073 nM. Compound c replaces the benzene with thiophene, leading to a predicted improvement of 3 kcal/mol and a measured improvement in IC50 by a factor of 78.

Figure 23:
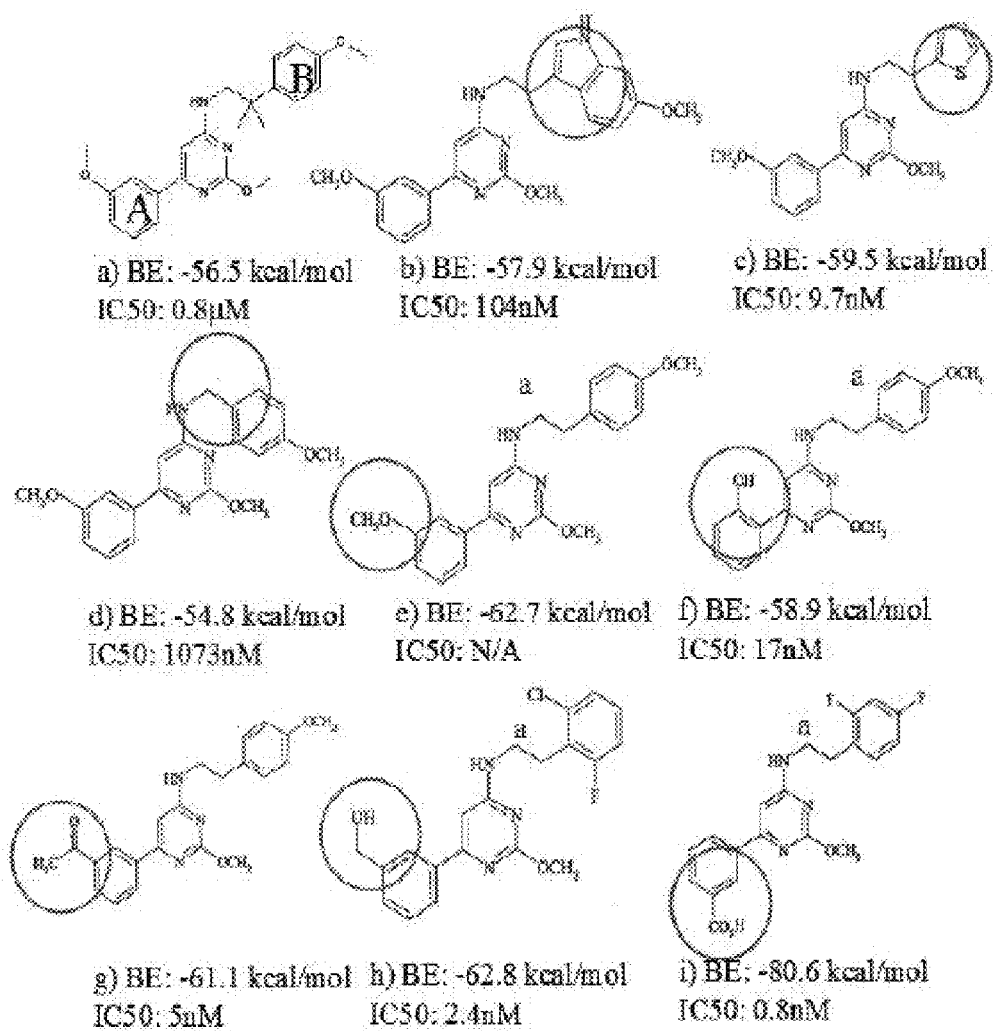
FIG. 23 shows modified pyrimidine compounds, all based on molecule a, shown in FIG. 22.

Compounds e to i have modifications on ring A. Substitutions with carbonic acid or other similar groups were predicted to lead to substantial improvements in binding due to favorable interaction with R310(7). These compounds were also found experimentally to have improved binding affinity (IC50) as shown in FIG. 23. Indeed the best compound i from the theory has the best-observed binding, with IC50=0.8 nM, 1000 times better than the starting compound a. In addition, the compounds predicted to be $2^{nd}$ best, $3^{rd}$ best etc. are in exactly the same sequence as in the experiments.

Example 9

Exemplary PTU Derivatives

For a sustained activation of bitter taste receptors in the GI system it is desirable that the bitter receptor ligand (e.g., a PTU derivative) remain in the GI system and not get absorbed. This requires ligands with altered pharmacokinetic properties like absorption, distribution, metabolism, excretion and toxicology.

Based on the PTU binding site in hTAS2R38$_{PAV}$ (FIG. 8), it was observed that the propyl group is exposed and not interacting with the receptor. This suggests that this functional group can be potentially used to attach to complementary molecules like amino acids, peptides, polyethylene glycols (PEGs), or saccharides.

Shown in FIG. 11 is a chemical formula of PTU (C7H10N2OS), the seven carbon atoms are denoted by the numbers 1 through 7. The sulfur, nitrogen and oxygen atoms are denoted S, N, and O, respectively. Carbon atoms 1, 2, and 3 form a chain that attaches to carbon atom 4. Carbon atoms 2 and 3 each have two hydrogen atoms and carbon atom 1 has three hydrogen atoms. One of the these three hydrogen atoms can be replaced by an OH functional group or the propyl group can be functionalized with a carboxylic acid or azide group to form a covalent bond to an amino acid, peptide, PEGs, monosaccharide, oligosaccharide or other suitable complementary molecules.

Figure 12:
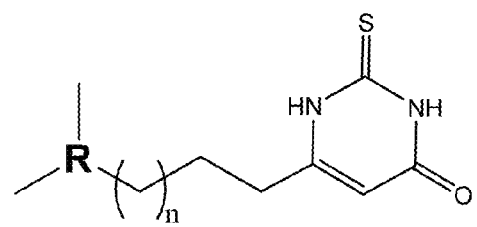
FIG. 12 shows PTU attached to a complementary molecule (R).
Figure 13:
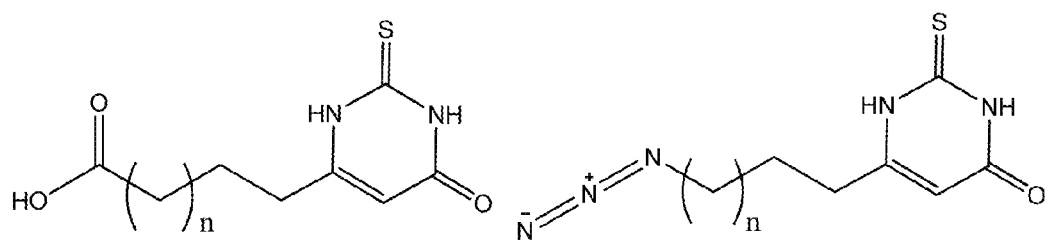
FIG. 13 shows PTU functionalized with a carboxylic acid group or an azide to ease linking to a complementary molecule like cellulose or PEG.
Figure 14:
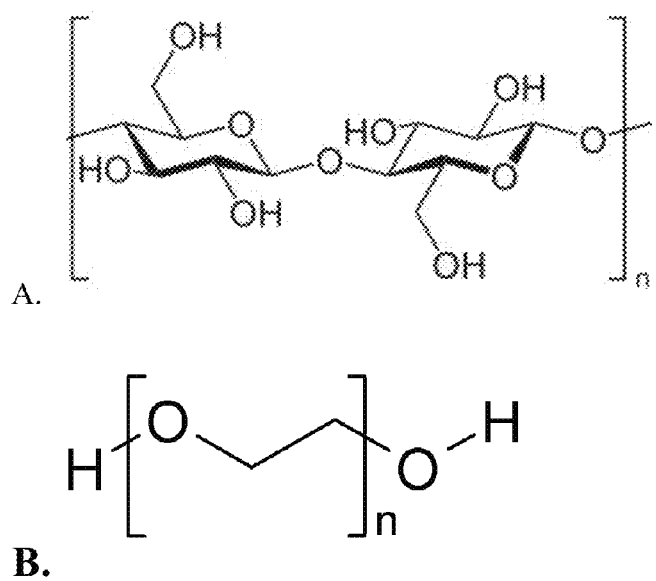
FIG. 14 shows Examples of R groups that can be attached to PTU: A. Cellulose; B. PEG.
Figure 15:
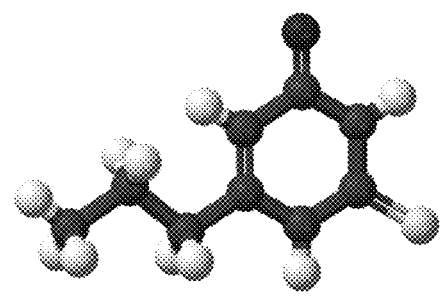
FIG. 15 shows the atomic structure of PTU as an agent according to an embodiment using an alternative notation, denoting the nitrogen, sulfur, and oxygen atoms, respectively, as N, S, and O.
Figure 16:
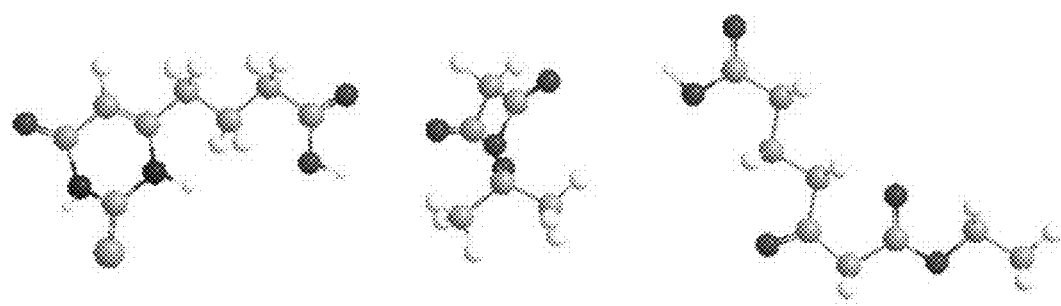
FIG. 16 shows the atomic structure of PTU-cellulose.
Figure 17:
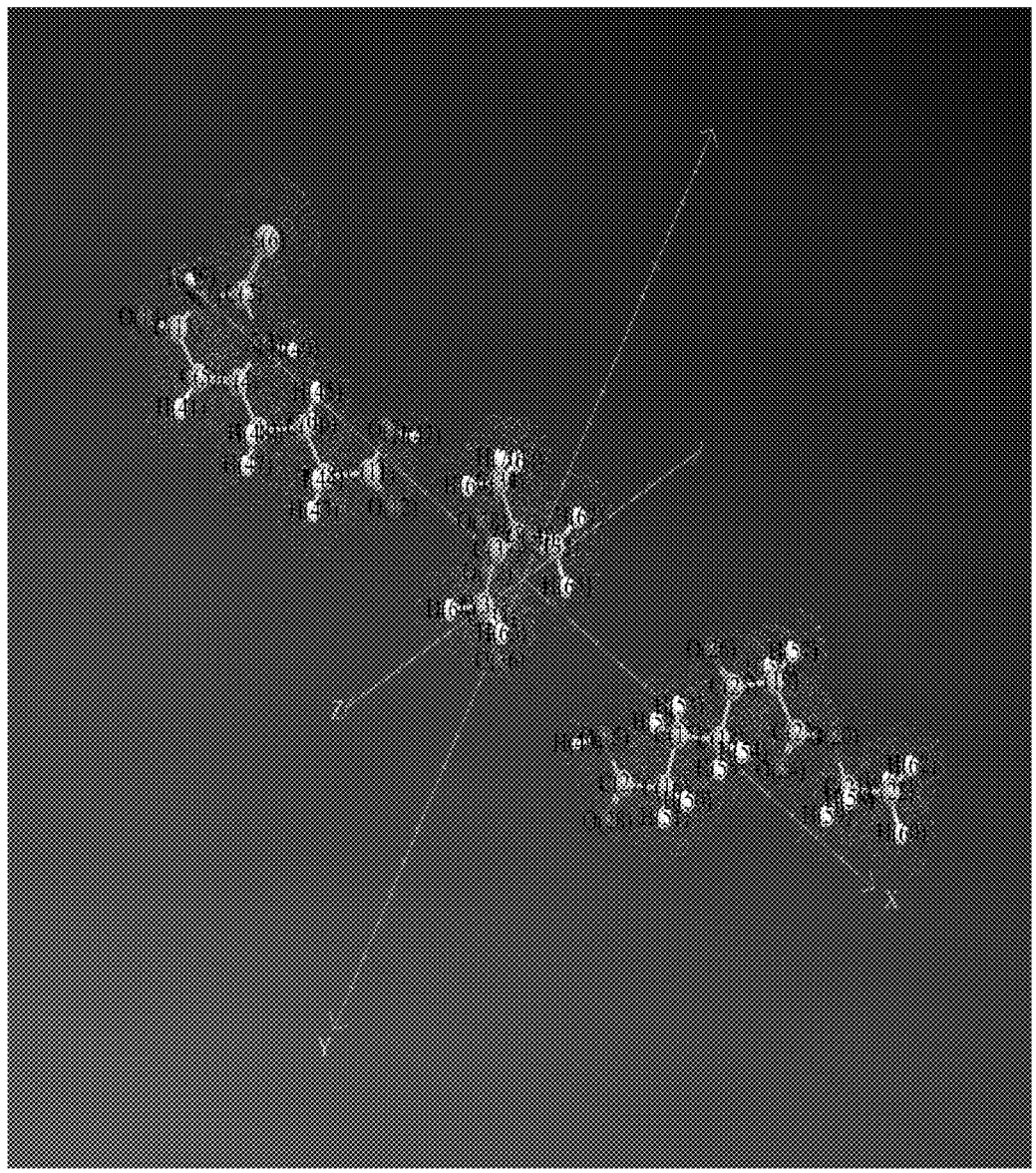
FIG. 17 shows the three dimensional view of the atomic structure of PTU-cellulose from a first angle.
Figure 18:
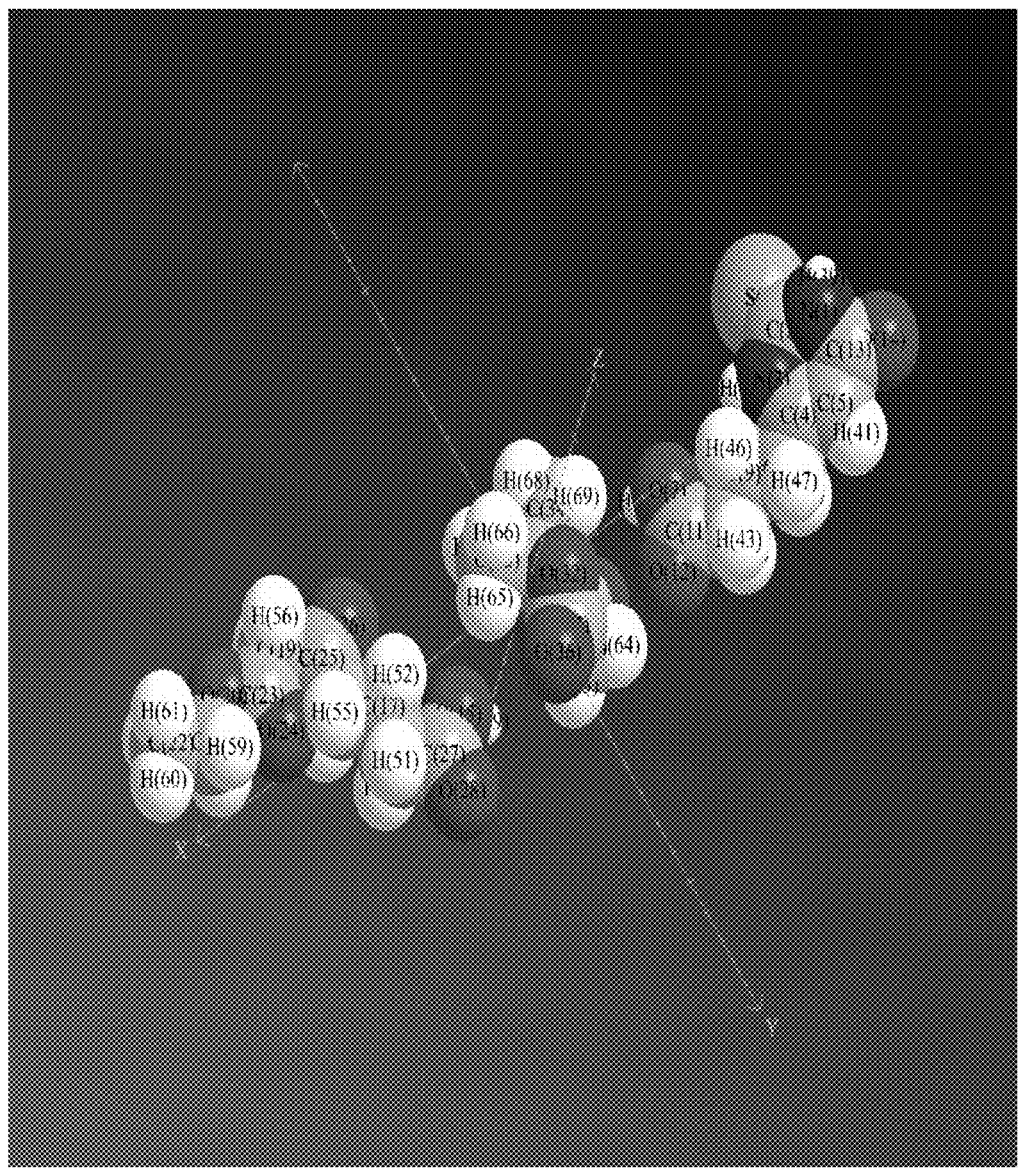
FIG. 18 shows the three dimensional view of the atomic structure of PTU-cellulose from a second angle.

Shown in FIG. 12 is PTU attached to an arbitrary R functional group through a linker of length n, where n can take a value in the range 1-20. This attachment is practically facilitated by first functionalizing PTU with reactive groups like carboxylic acid and azide (FIG. 13). These reactive groups enable attaching large molecules like cellulose and PEGs (FIG. 14) to PTU to produce PTU derivatives with desirable pharmacokinetic properties.

It has been shown that intestinal permeability of PEGs is highly dependent on their molecular weight [Kerckhoffs 2010]. This provides a lower limit of 10,000 for PEG's molecular weight, which will keep, e.g., PTU coupled to this PEG, in the GI system for a prolonged activation of bitter taste receptors in the gut resulting in a sustained modulation of the hormone release.

Example 10

Preparation of Active Agent Conjugated with a Complementary Molecule: PTU-cellulose An active agent conjugated with a suitable complementary molecule can be prepared using known methods. An exemplary reaction scheme for conjugation with a suitable complementary molecule. In the example below shows chemical synthesis of PTU-cellulose.

Scheme Synthetic route for PTU-Cellulose conjugate

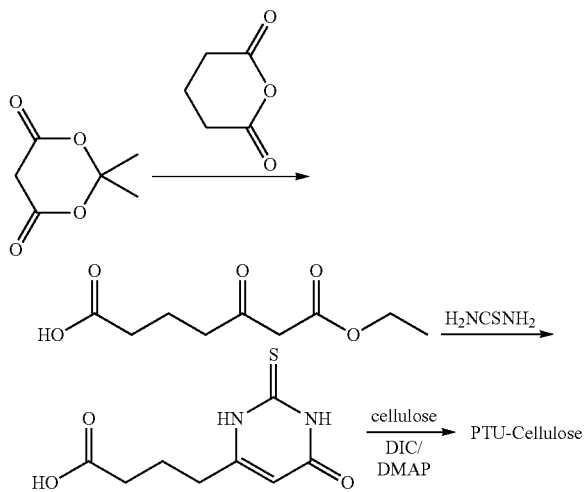

One of PTU's pharmacokinetic properties (distribution) was modified through conjugation to cellulose. This and other modifications can modify PTU's full pharmacokinetic profile (Absorption, Distribution, Metabolism, Excretion, and Toxicology).

Example 11

PTC Administration Results in an Increased Release of PYY

Applicants administered either 5 ml of saline or 5 mM PTC in 5 ml of saline into the stomachs of fasting conscious male Sprague-Dawley rats (250-300 gm in weight) by standard gastric gavage. The rats were then euthanized 45 min later and removed blood via intracardiac puncture and measured PYY in the blood by a recently modified radioimmunoassay using CURE antibody 9153 (Gift of J Reeve, University of California, Los Angeles.). Results demonstrated a doubling of PYY levels as follows: Saline gavaged rats (n=5) 71+/−35 pM, PTC gavaged rats (n=5) 154+/−44 pM. An interesting observation at time of sacrifice of the rats was that the volume of fluid remaining in the stomachs of the PTC-treated rats ranged from 1-2 ml whereas there was less than 0.5 ml in the stomach of saline-treated rats. This observation suggests that PTC through interaction with TAS2R38 regulates gastric emptying.

Example 12

PTC Administration Results in GLP-1 Release in Endocrine Cells

In order to determine the feasibility of a cell-based system for investigating the selectivity of ligands for a particular bitter taste receptor, Applicants chose STC-5 cells and measured the effect of PTC on GLP-1 from these cells. Applicants have demonstrated that STC-5 cells have TAS2R38 among several other bitter taste receptors.

In GLP-1 release experiments, selected endocrine cell lines of STC-5 cells or NCI-H716 cells were used for testing release of GLP-1 triggered by various possible ligands. Endocrine cells were incubated in serum-free DME/F12 media containing vehicle (0.01% DMSO) and a candidate ligand of certain concentration and for a certain period of incubation time. After incubation, secretion active GLP-1 in media was measured with GLP-1 RIA kit (Linco Research®, Missouri, USA).

In particular, STC-5 cells were incubated for 30 minutes in serum-free DME/F12 media containing vehicle (0.01% DMSO) and PTC at the indicated concentrations. Secretion of active GLP-1 in media was measured with GLP-1 RIA kit (Linco Research, Missouri, USA). The experiments for all groups have been conducted in duplicates.

Figure 24A:
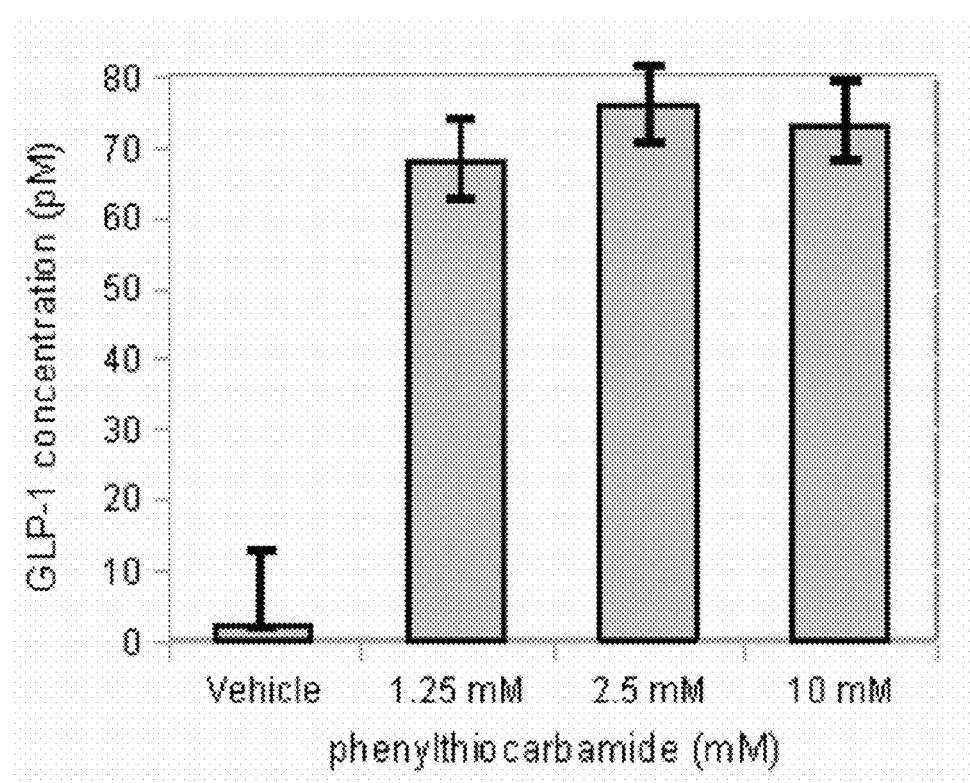
FIG. 24A shows GLP-1 release from endocrine STC-5 cells triggered by PTC at various concentrations. The X-axis indicates the concentration of PTC used in cell incubation in mM; the Y-axis shows the amount of GLP-1 release in pM. Each bar represents an average value obtained from duplicates.
Figure 24B:
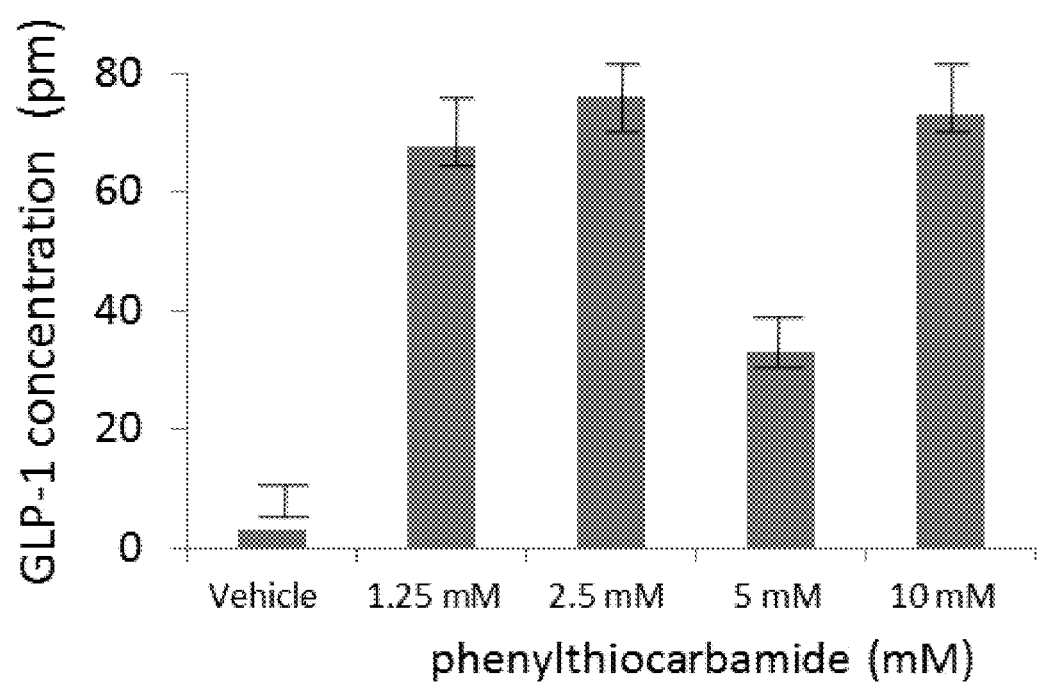
FIG. 24B shows GLP-1 release from endocrine STC-5 cells triggered by PTC at various concentrations. The X-axis indicates the concentration of PTC used in cell incubation in mM; the Y-axis shows the amount of GLP-1 release in pM. Each bar represents an average value obtained from duplicates.

The results illustrated in FIGS. 24A and 24B show that PTC had a large effect on GLP-1 release from these cells, while the vehicle (negative control or PTC concentration of 0) does not. This shows that bitter ligands like GLP-1 can be effectively used for the release of GLP-1.

Example 13

Glucagon-like Peptide-1 (GLP-1) Release from Endocrine Cell Line, NCI-H716 Cells Endocrine cell lines of NCI-H716 cells were used for testing release of GLP-1 triggered by various possible ligands.

NCI-H716 cells were incubated in serum-free DME/F12 media containing vehicle (0.01% DMSO) with a candidate ligand at the indicated concentrations. Secretion active GLP-1 in media was measured with GLP-1 RIA kit (Linco Research, Missouri, USA). The results were summarized in Table 2. The experiments for all groups have been conducted in duplicates.

TABLE 2

GLP-1 release by NCI-H716 cells triggered by various ligands.

| Groups | Concentration | GLP-1 (pmol/mg protein) |
|---|---|---|
| Control | 0 | 58.47 |
| PTC | 2.5 μm | 98.73 |
| Butyrate | 2.5 mM | 100.77 |
| Glycyrrhizic acid ammonium salt | 10 μm | 71.95 |
| Epigallocatechin gallate | 1 μm | 91.15 |
| Ginseng Root | 10 μm | 62.21 |
| Hyperforin | 5 μg/ml | 104.87 |
| Berberine chloride | 10 μm | 86.41 |
| Coptisine chloride | 10 μm | 121.35 |
| Allyl methyl sulfide | 10 μm | 91.547 |
| Hops (Hopsteiner BetaBio45) | 10 μm | 86.149 |
| Rottlerin | 0.05% | 111.18 |
| Curcumin | 10 μm | 61.52 |
| Ellagic acid | 10 μm | 77.25 |
| Embelin | 10 μm | 83.55 |

PTRU, Epigallocatechin and Berberine choloride are exemplary bitter tastant receptor ligands that are also bitter tastants. Hopsteiner is an exemplary combination of ligands which results in a bitter tastants combination. Ginseng root is an exemplary combination of bitter tastant receptor ligands including many, many different components. The remaining ligands are not bitter tastants. The results illustrated in Table 2 show that PTC, butyrate, glycyrrhizic acid, epigallocatechin gallate, hyperforin, berberine, coptisine, ally sulfide, the B-acids in hops (Hopsteiner BetaBio45 composition), rottlerin, ellagic acid and embelin each increase the release of GLP-1 from NCI-H716 cells, a model cell line representing the L-cell.

Examples 14

Endocrine Cells Presenting Bitter Tastant Receptor and Related Hormones

Exemplary endocrine cells expected or known to present bitter tastant receptor ligands are listed in the following Table 3 together with the specific metabolic hormones associated with each of those different GI cells.

TABLE 3

Types of enteroendocrine cells and their secreted products

| Cell Type | Secreted hormone | Location |
|---|---|---|
| α cells | Glucagon | Pancreas (Islets of Langerhans) |
| β cells | Insulin, Islet amyloid, polypeptide | Pancreas (Islets of Langerhans) |
| PP cells | Pancreatic polypeptide | Pancreas (Islets of Langerhans) |
| δcells (D cell) | Somatostatin | Pancreas (Islets of Langerhans) |
| cells | Gastrin | Stomach - Occasionally in pancreas |
| X/A-like cells | Ghrelin, nesfatin-1 | Stomach - Occasionally in pancreas |
| GIP cells (K cells) | GIP, xenin | Small intestine |
| S cells | Secretin | Small intestine |
| I cells (CCK cells) | Cholecystokinin | Small intestine |
| N cells | Neurotensin | Small intestine |
| L cells | PYY, GLP-1,GLP-2,oxyntomodulin | Small and large intestine |

Abbreviations: CCK, cholecystokinin; GIP, gastric inhibitory polypeptide; GLP, glucagon-like peptide; PPY, peptide YY.
From Field, B.C.T. et al. Bowels control brain: gut hormones and obesity *Nat. Rev. Endocrinal*, 2010; 6:444-453.

Example 15

Selection of Complementary Molecule for a Certain Ligand

In order to select an appropriate complementary molecule to be tethered to a determined ligand, it is expected that the ligand can be tethered to a molecule of a size that has a minimum weight determined with reference to the existing literature. One skilled in the art would know or be able to find in the literature that certain molecular weights of PEG will be unlikely to leave the lumen of the intestine. Thus, those molecular weights and greater are those one would use for a complementary molecule to be conjugated to ligands intended to bind GI bitter taste receptors and not to be absorbed across the lumen of the intestine.

In one aspect, one skilled in the art could consult a study (Kerckhoffs) of IBS patients (and comparing to healthy patients) testing molecular masses M (sub r) of 400, 1500, 4000 and 10,000 and showing that under certain conditions the 10,000 weight PEG migrated out of the intestine (present in urine) in 7%-33% of the (small) study population. It is not clear that a 10,000 weight PEG would escape in a non-IBS patient, suggesting that for that population lower weight might suffice, but it is possible that for both IBS and non-IBS groups, a complementary PEG of a greater weight would likely be preferable.

Accordingly, the molecular weight of a molecule intended to keep the agent in the intestine here it is expected to be in the range of 10,000 or greater. In this case the tethered molecule, whether PEG or other, and the tether, are expected to both have to be resistant or impervious to degradation by the digestive enzymes or other chemicals and action of the stomach and intestine. The tether would have to be connected to the agent in a way and/or at such a point on the agent that it does not interfere with/inhibit the agent's functioning/binding. Modification by attaching to cellulose or PEG is expected to accomplish this effect.

The examples set forth above are provided to give those of ordinary skill in the art a complete disclosure and description of how to make and use the embodiments of the arrangements, devices, ligands, agents, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing filed herein is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

Bray J K and Goddard W A (2008). The structure of human serotonin 2c G protein-coupled receptor bound to agonists and antagonists, *J Mol Graph Model* 27:66-81.

Bufe B et al. (2005). The Molecular Basis of Individual Differences in Phenylthiocarbamide and Propylthiouracil Bitterness Perception, *Curr Biol* 15:322-7.

de Jong L A et al. (2005). Receptor-ligand binding assays: technologies and applications, *J Chromatogr B Analyt Technol Biomed Life Sci* 829:1-25.

Farrens D et al. (1996). Requirement of rigid-body motion of transmembrane helices for light activation of rhodopsin, *Science* 274:768-70.

Field B C T et al. (2010). Bowels control brain: gut hormones and obesity, *Nature Rev Endocrin* 6:444-53.

Goddard W A et al. (2010). Predicted 3D structures for adenosine receptors bound to ligands: Comparison to the crystal structure, *J Struc Biol* 170:10-20.

Kam V W T and Goddard W A (2008). Flat-bottom strategy for improved accuracy in protein side-chain placements, *J Chem Theor Comput* 4:2160-9.

Kenakin T and Miller L J (2010). Seven Transmembrane Receptors as Shapeshifting Proteins: The Impact of Allosteric Modulation and Functional Selectivity on New Drug Discovery, *Pharmacol Rev* 62:265-304.

Keravis T and Lugnier C (2010). Cyclic nucleotide phosphodiesterases (PDE) and peptide motif, *Curr Pharm Des* 16:1114-25.

Kerckhoffs A P et al. (2010). Intestinal permeability in irritable bowel syndrome patients: effects of NSAIDs, *Dig Dis Sci* 55:716-23.

Kuntz I D et al. (1982). A geometric approach to macromolecule-ligand interactions, *J Mol Biol* 161:269-288.

Lefkowitz R J et al. (1970). Radioreceptor assay of adrenocorticotropic hormone: new approach to assay of polypeptide hormones in plasma, *Science* 170:633-5.

Li Y et al. (2007). Prediction of the 3D structure and dynamics of human DP G-protein coupled receptor bound to an agonist and an antagonist, *J Am Chem Soc* 129:10720-31.

Lim K T et al. (1997). Molecular dynamics for very large systems on massively parallel computers: The MPSim program, *J Comput Chem* 18:501-521.

Mayo S L et al. (1990). DREIDING: a generic force field for molecular simulations, *J Phys Chem* 94:8897-909.

Phillips J C et al. (2005). Scalable molecular dynamics with NAMD, *J Comput Chem* 26:1781-1802.

Pronin A N et al. (2004). Identification of Ligands for two human bitter T2R receptors, *Chem Senses* 29:583-93.

Scanziani M and Hausser M (2009). Electrophysiology in the age of light, *Nature* 461:930-9.

Schultz S G (1998). A century of (epithelial) transport physiology: from vitalism to molecular cloning. *Am J Physiol Cell Physiol* 274:C13-23.

Tsien R Y (2003). Imagining imaging's future, *Nat Rev Mol Cell Biol* Suppl S:SS16-21.

Wong G T et al. (1996). Transduction of bitter and sweet taste by gustducin, *Nature* 381:796-800.

Zacharias D A et al. (2000). Recent advances in technology for measuring and manipulating cell signals, *Curr Opin Neurobiol* 10:416-21.

Zhang J et al. (2002). Creating new fluorescent probes for cell biology, *Nat Rev Mol Cell Biol* 3:906-18.

SEQUENCE LISTING

```
<160> NUMBER OF SEQ ID NOS: 26

<210> SEQ ID NO 1
<211> LENGTH: 313
<212> TYPE: PRT
<213> ORGANISM: Turkey

<400> SEQUENCE: 1

Met Gly Ala Glu Leu Leu Ser Gln Gln Trp Glu Ala Gly Met Ser Leu
1               5                   10                  15

Leu Met Ala Leu Val Val Leu Leu Ile Val Ala Gly Asn Val Leu Val
            20                  25                  30

Ile Ala Ala Ile Gly Ser Thr Gln Arg Leu Gln Thr Leu Thr Asn Leu
        35                  40                  45

Phe Ile Thr Ser Leu Ala Cys Ala Asp Leu Val Val Gly Leu Leu Val
    50                  55                  60

Val Pro Phe Gly Ala Thr Leu Val Val Arg Gly Thr Trp Leu Trp Gly
65                  70                  75                  80

Ser Phe Leu Cys Glu Leu Trp Thr Ser Leu Asp Val Leu Cys Val Thr
```

```
            85                  90                  95
Ala Ser Ile Glu Thr Leu Cys Val Ile Ala Ile Asp Arg Tyr Leu Ala
            100                 105                 110

Ile Thr Ser Pro Phe Arg Tyr Gln Ser Leu Met Thr Arg Ala Arg Ala
            115                 120                 125

Lys Val Ile Ile Cys Thr Val Trp Ala Ile Ser Ala Leu Val Ser Phe
        130                 135                 140

Leu Pro Ile Met Met His Trp Trp Arg Asp Glu Asp Pro Gln Ala Leu
145                 150                 155                 160

Lys Cys Tyr Gln Asp Pro Gly Cys Cys Asp Phe Val Thr Asn Arg Ala
                165                 170                 175

Tyr Ala Ile Ala Ser Ser Ile Ile Ser Phe Tyr Ile Pro Leu Leu Ile
            180                 185                 190

Met Ile Phe Val Ala Leu Arg Val Tyr Arg Glu Ala Lys Glu Gln Ile
        195                 200                 205

Arg Lys Ile Asp Arg Ala Ser Lys Arg Lys Val Met Leu Met Arg
    210                 215                 220

Glu His Lys Ala Leu Lys Thr Leu Gly Ile Ile Met Gly Val Phe Thr
225                 230                 235                 240

Leu Cys Trp Leu Pro Phe Phe Leu Val Asn Ile Val Asn Val Phe Asn
                245                 250                 255

Arg Asp Leu Val Pro Asp Trp Leu Phe Val Ala Phe Asn Trp Leu Gly
            260                 265                 270

Tyr Ala Asn Ser Ala Met Asn Pro Ile Ile Tyr Cys Arg Ser Pro Asp
        275                 280                 285

Phe Arg Lys Ala Phe Lys Arg Leu Leu Ala Phe Pro Arg Lys Ala Asp
    290                 295                 300

Arg Arg Leu His His His His His His
305                 310

<210> SEQ ID NO 2
<211> LENGTH: 333
<212> TYPE: PRT
<213> ORGANISM: Homo sapiens

<400> SEQUENCE: 2

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
            20                  25                  30

Asn Ala Phe Val Phe Leu Val Asn Phe Trp Asp Val Val Lys Arg Gln
        35                  40                  45

Pro Leu Ser Asn Ser Asp Cys Val Leu Leu Cys Leu Ser Ile Ser Arg
    50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

Leu Ile Cys Leu Ala Ser Trp Val Ser Arg Lys Ile Ser Gln Met Leu
    130                 135                 140
```

```
Leu Gly Ile Ile Leu Cys Ser Cys Ile Cys Thr Val Leu Cys Val Trp
145                 150                 155                 160

Cys Phe Phe Ser Arg Pro His Phe Thr Val Thr Val Leu Phe Met
                165                 170                 175

Asn Asn Asn Thr Arg Leu Asn Trp Gln Ile Lys Asp Leu Asn Leu Phe
            180                 185                 190

Tyr Ser Phe Leu Phe Cys Tyr Leu Trp Ser Val Pro Pro Phe Leu Leu
        195                 200                 205

Phe Leu Val Ser Ser Gly Met Leu Thr Val Ser Leu Gly Arg His Met
    210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
                245                 250                 255

Val Ile Ser Ser Cys Ala Ala Phe Ile Ser Val Pro Leu Leu Ile Leu
            260                 265                 270

Trp Arg Asp Lys Ile Gly Val Met Val Cys Val Gly Ile Met Ala Ala
        275                 280                 285

Cys Pro Ser Gly His Ala Ala Val Leu Ile Ser Gly Asn Ala Lys Leu
    290                 295                 300

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                325                 330

<210> SEQ ID NO 3
<211> LENGTH: 333
<212> TYPE: PRT
<213> ORGANISM: Homo sapiens

<400> SEQUENCE: 3

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
                20                  25                  30

Asn Ala Phe Val Phe Leu Val Asn Phe Trp Asp Val Val Lys Arg Gln
            35                  40                  45

Ala Leu Ser Asn Ser Asp Cys Val Leu Leu Cys Leu Ser Ile Ser Arg
        50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

Leu Ile Cys Leu Ala Ser Trp Val Ser Arg Lys Ile Ser Gln Met Leu
    130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Val Leu Phe Met
                165                 170                 175

Asn Asn Asn Thr Arg Leu Asn Trp Gln Ile Lys Asp Leu Asn Leu Phe
            180                 185                 190
```

```
Tyr Ser Phe Leu Phe Cys Tyr Leu Trp Ser Val Pro Pro Phe Leu Leu
        195                 200                 205

Phe Leu Val Ser Ser Gly Met Leu Thr Val Ser Leu Gly Arg His Met
210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
                245                 250                 255

Val Ile Ser Ser Cys Val Ala Phe Ile Ser Val Pro Leu Leu Ile Leu
                260                 265                 270

Trp Arg Asp Lys Ile Gly Val Met Val Cys Val Gly Ile Met Ala Ala
                275                 280                 285

Cys Pro Ser Gly His Ala Ala Ile Leu Ile Ser Gly Asn Ala Lys Leu
                290                 295                 300

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                325                 330
```

<210> SEQ ID NO 4
<211> LENGTH: 333
<212> TYPE: PRT
<213> ORGANISM: Homo sapiens

<400> SEQUENCE: 4

```
Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
                20                  25                  30

Asn Ala Phe Val Phe Leu Val Asn Phe Trp Asp Val Val Lys Arg Gln
                35                  40                  45

Ala Leu Ser Asn Ser Asp Cys Val Leu Leu Cys Leu Ser Ile Ser Arg
        50                  55                  60

Leu Phe Leu His Gly Leu Leu Phe Leu Ser Ala Ile Gln Leu Thr His
65              70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
                100                 105                 110

Leu Ser Leu Leu Tyr Cys Ser Lys Leu Ile Arg Phe Ser His Thr Phe
        115                 120                 125

Leu Ile Cys Leu Ala Ser Trp Val Ser Arg Lys Ile Ser Gln Met Leu
130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Thr Val Leu Phe Met
                165                 170                 175

Asn Asn Asn Thr Arg Leu Asn Trp Gln Ile Lys Asp Leu Asn Leu Phe
                180                 185                 190

Tyr Ser Phe Leu Phe Cys Tyr Leu Trp Ser Val Pro Pro Phe Leu Leu
        195                 200                 205

Phe Leu Val Ser Ser Gly Met Leu Thr Val Ser Leu Gly Arg His Met
210                 215                 220

Arg Thr Met Lys Val Tyr Thr Arg Asn Ser Arg Asp Pro Ser Leu Glu
```

```
                225                 230                 235                 240
Ala His Ile Lys Ala Leu Lys Ser Leu Val Ser Phe Phe Cys Phe Phe
                245                 250                 255

Val Ile Ser Ser Cys Ala Ala Phe Ile Ser Val Pro Leu Leu Ile Leu
                260                 265                 270

Trp Arg Asp Lys Ile Gly Val Met Val Cys Val Gly Ile Met Ala Ala
                275                 280                 285

Cys Pro Ser Gly His Ala Ala Ile Leu Ile Ser Gly Asn Ala Lys Leu
                290                 295                 300

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                325                 330

<210> SEQ ID NO 5
<211> LENGTH: 333
<212> TYPE: PRT
<213> ORGANISM: Homo sapiens

<400> SEQUENCE: 5

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
                20                  25                  30

Asn Ala Phe Val Phe Leu Val Asn Phe Trp Asp Val Val Lys Arg Gln
                35                  40                  45

Pro Leu Ser Asn Ser Asp Cys Val Leu Leu Cys Leu Ser Ile Ser Arg
                50                  55                  60

Leu Phe Leu His Gly Leu Leu Phe Leu Ser Ala Ile Gln Leu Thr His
65              70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
                100                 105                 110

Leu Ser Leu Leu Tyr Cys Ser Lys Leu Ile Arg Phe Ser His Thr Phe
                115                 120                 125

Leu Ile Cys Leu Ala Ser Trp Val Ser Arg Lys Ile Ser Gln Met Leu
                130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Thr Val Leu Phe Met
                165                 170                 175

Asn Asn Asn Thr Arg Leu Asn Trp Gln Ile Lys Asp Leu Asn Leu Phe
                180                 185                 190

Tyr Ser Phe Leu Phe Cys Tyr Leu Trp Ser Val Pro Pro Phe Leu Leu
                195                 200                 205

Phe Leu Val Ser Ser Gly Met Leu Thr Val Ser Leu Gly Arg His Met
                210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
                245                 250                 255

Val Ile Ser Ser Cys Val Ala Phe Ile Ser Val Pro Leu Leu Ile Leu
                260                 265                 270
```

```
Trp Arg Asp Lys Ile Gly Val Met Val Cys Val Gly Ile Met Ala Ala
            275                 280                 285

Cys Pro Ser Gly His Ala Ala Val Leu Ile Ser Gly Asn Ala Lys Leu
            290                 295                 300

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                325                 330

<210> SEQ ID NO 6
<211> LENGTH: 31
<212> TYPE: PRT
<213> ORGANISM: Homo sapiens

<400> SEQUENCE: 6

Phe Leu Pro Ile Ile Phe Ser Ile Leu Ile Val Val Ile Phe Val Ile
1               5                   10                  15

Gly Asn Phe Ala Asn Gly Phe Ile Ala Leu Val Asn Ser Ile Glu
            20                  25                  30

<210> SEQ ID NO 7
<211> LENGTH: 29
<212> TYPE: PRT
<213> ORGANISM: Homo sapiens

<400> SEQUENCE: 7

Asp Gln Ile Leu Thr Ala Leu Ala Val Ser Arg Val Gly Leu Leu Trp
1               5                   10                  15

Val Leu Leu Leu His Trp Tyr Ala Thr Gln Leu Asn Pro
            20                  25

<210> SEQ ID NO 8
<211> LENGTH: 29
<212> TYPE: PRT
<213> ORGANISM: Homo sapiens

<400> SEQUENCE: 8

Arg Ile Thr Ala Tyr Asn Val Trp Ala Val Thr Asn His Phe Ser Ser
1               5                   10                  15

Trp Leu Ala Thr Ser Leu Ser Met Phe Tyr Leu Leu Arg
            20                  25

<210> SEQ ID NO 9
<211> LENGTH: 26
<212> TYPE: PRT
<213> ORGANISM: Homo sapiens

<400> SEQUENCE: 9

Lys Ser Val Val Leu Val Ile Leu Leu Gly Pro Leu Phe Leu Val
1               5                   10                  15

Cys His Leu Phe Val Ile Asn Met Asp Glu
            20                  25

<210> SEQ ID NO 10
<211> LENGTH: 31
<212> TYPE: PRT
<213> ORGANISM: Homo sapiens

<400> SEQUENCE: 10

His Ser Asn Met Thr Leu Thr Met Leu Ala Asn Phe Val Pro Leu Thr
1               5                   10                  15
```

```
Leu Thr Leu Ile Ser Phe Leu Leu Ile Cys Ser Leu Cys Lys
            20                  25                  30
```

<210> SEQ ID NO 11
<211> LENGTH: 28
<212> TYPE: PRT
<213> ORGANISM: Homo sapiens

<400> SEQUENCE: 11

```
Lys Ala Leu Gln Thr Val Thr Ser Phe Leu Leu Cys Ala Ile Tyr
1               5                   10                  15
Phe Leu Ser Met Ile Ile Ser Val Cys Asn Leu Gly
            20                  25
```

<210> SEQ ID NO 12
<211> LENGTH: 24
<212> TYPE: PRT
<213> ORGANISM: Homo sapiens

<400> SEQUENCE: 12

```
Pro Val Phe Met Phe Cys Gln Ala Ile Ile Phe Ser Tyr Pro Ser Thr
1               5                   10                  15
His Pro Phe Ile Leu Ile Leu Gly
            20
```

<210> SEQ ID NO 13
<211> LENGTH: 31
<212> TYPE: PRT
<213> ORGANISM: Homo sapiens

<400> SEQUENCE: 13

```
Glu Val Arg Ser Thr Phe Leu Phe Ile Ser Val Leu Glu Phe Ala Val
1               5                   10                  15
Gly Phe Leu Thr Asn Ala Phe Val Phe Leu Val Asn Phe Trp Asp
            20                  25                  30
```

<210> SEQ ID NO 14
<211> LENGTH: 31
<212> TYPE: PRT
<213> ORGANISM: Rattus norvegicus

<400> SEQUENCE: 14

```
Glu Ala Lys Ile Ser Phe Leu Phe Leu Ser Val Val Glu Phe Ala Val
1               5                   10                  15
Gly Ile Met Ala Asn Ala Phe Ile Val Leu Val Asn Phe Trp Asp
            20                  25                  30
```

<210> SEQ ID NO 15
<211> LENGTH: 30
<212> TYPE: PRT
<213> ORGANISM: Homo sapiens

<400> SEQUENCE: 15

```
Lys Gln Phe His Thr Leu Gln Ile Ala Ser Leu Phe Leu Leu Gly His
1               5                   10                  15
Leu Phe Leu Arg Ser Ile Ser Leu Cys Leu Leu Val Cys Asp
            20                  25                  30
```

<210> SEQ ID NO 16
<211> LENGTH: 29
<212> TYPE: PRT
<213> ORGANISM: Rattus norvegicus

```
<400> SEQUENCE: 16

Gln Phe Cys Ala Leu Gln Ile Ala Asp Leu Leu Leu Gly Gln Leu
1               5                   10                  15

Phe Leu Arg Thr Ile Ser Leu Cys Leu Leu Ala Ile Asp
            20                  25

<210> SEQ ID NO 17
<211> LENGTH: 44
<212> TYPE: PRT
<213> ORGANISM: Homo sapiens

<400> SEQUENCE: 17

His Ser Tyr Gln Ala Ile Ile Met Leu Trp Met Ile Ala Asn Gln Ala
1               5                   10                  15

Asn Leu Trp Leu Ala Ala Cys Leu Ser Leu Leu Tyr Cys Ser Lys Leu
            20                  25                  30

Ile Arg Phe Ser His Thr Phe Leu Ile Cys Leu Ala
            35                  40

<210> SEQ ID NO 18
<211> LENGTH: 40
<212> TYPE: PRT
<213> ORGANISM: Rattus norvegicus

<400> SEQUENCE: 18

Ala Ile Leu Thr Leu Trp Met Ser Ala Asn Gln Val Ser Leu Trp Leu
1               5                   10                  15

Ala Ala Cys Leu Ser Leu Leu Tyr Cys Ala Lys Ile Val Arg Phe Ser
            20                  25                  30

His Thr Phe Pro Leu His Leu Ala
            35                  40

<210> SEQ ID NO 19
<211> LENGTH: 28
<212> TYPE: PRT
<213> ORGANISM: Homo sapiens

<400> SEQUENCE: 19

Arg Ser Phe Phe Cys Trp Val Cys Leu Val Thr Cys Ile Cys Ser Cys
1               5                   10                  15

Leu Ile Ile Gly Leu Leu Met Gln Ser Ile Lys Arg
            20                  25

<210> SEQ ID NO 20
<211> LENGTH: 24
<212> TYPE: PRT
<213> ORGANISM: Rattus norvegicus

<400> SEQUENCE: 20

Asp Trp Leu Cys Leu Ala Thr Cys Val Gly Ser Phe Leu Leu Ala Val
1               5                   10                  15

Leu Leu Met Gln Leu Phe Arg Arg
            20

<210> SEQ ID NO 21
<211> LENGTH: 34
<212> TYPE: PRT
<213> ORGANISM: Homo sapiens

<400> SEQUENCE: 21

Asp Leu Asn Leu Phe Tyr Ser Phe Leu Phe Cys Tyr Leu Trp Ser Val
```

```
                1               5                   10                  15
            Pro Pro Phe Leu Leu Phe Leu Val Ser Ser Gly Met Leu Thr Val Ser
                        20                  25                  30

Leu Gly

<210> SEQ ID NO 22
<211> LENGTH: 34
<212> TYPE: PRT
<213> ORGANISM: Rattus norvegicus

<400> SEQUENCE: 22

Lys Leu Asn Phe Phe Tyr Ser Phe Val Phe Cys Asn Val Gly Ser Val
            1               5                   10                  15

Pro Pro Ser Leu Val Phe Leu Ile Ser Ser Gly Val Leu Val Ile Ser
                        20                  25                  30

Leu Gly

<210> SEQ ID NO 23
<211> LENGTH: 23
<212> TYPE: PRT
<213> ORGANISM: Homo sapiens

<400> SEQUENCE: 23

Leu Pro Val Ser Ile Phe Ala Ala Cys Ser Ser Ile Val Phe Phe Cys
            1               5                   10                  15

Phe Phe Ser Val Leu Ser Lys
                        20

<210> SEQ ID NO 24
<211> LENGTH: 26
<212> TYPE: PRT
<213> ORGANISM: Rattus norvegicus

<400> SEQUENCE: 24

Leu Pro Ile Ser Ile Leu Ala Ala Cys Phe Ser Val Val Tyr Phe Cys
            1               5                   10                  15

Leu Phe Ser Val Leu Phe Ile Ile Ala Arg
                        20                  25

<210> SEQ ID NO 25
<211> LENGTH: 21
<212> TYPE: PRT
<213> ORGANISM: Homo sapiens

<400> SEQUENCE: 25

Met Val Cys Val Gly Ile Met Ala Ala Cys Pro Ser Gly His Ala Ala
            1               5                   10                  15

Ile Leu Ile Ser Gly
                        20

<210> SEQ ID NO 26
<211> LENGTH: 21
<212> TYPE: PRT
<213> ORGANISM: Rattus norvegicus

<400> SEQUENCE: 26

Met Val Cys Ile Gly Met Met Ala Ala Cys Pro Ser Gly His Ala Ala
            1               5                   10                  15

Ile Leu Ile Ser Gly
                        20
```

What is claimed is:

1. A composition comprising a combination of 6-n-propylthiouracil and a complementary molecule, wherein the complementary molecule interferes with systemic absorption and release of 6-n-propylthiouracil upon enteral administration, wherein the complementary molecule is polyethylene glycol, wherein the polyethylene glycol is conjugated to the 6-n-propylthiouracil, and wherein the combination results in prolonged activation of bitter taste receptors in the gut.

2. The composition of claim 1, wherein 6-n-propylthiouracil comprises a propyl group, and the complementary molecule is attached to the propyl group.

3. The composition of claim 1, wherein the polyethylene glycol has a molecular weight ($M_r$) of at least about 10,000 g/mol.

4. A composition comprising a combination of 6-n-propylthiouracil and a complementary molecule, wherein the complementary molecule interferes with systemic absorption and release of 6-n-propylthiouracil upon enteral administration, wherein the complementary molecule is cellulose, wherein the cellulose is conjugated to the 6-n-propylthiouracil, and wherein the combination results in prolonged activation of bitter taste receptors in the gut.

5. The composition of claim 4, wherein 6-n-propylthiouracil comprises a propyl group, and the complementary molecule is attached to the propyl group.

* * * * *

UNITED STATES PATENT AND TRADEMARK OFFICE
CERTIFICATE OF CORRECTION

PATENT NO. : 9,272,051 B2
APPLICATION NO. : 14/320159
DATED : March 1, 2016
INVENTOR(S) : William A. Goddard, III et al.

Page 1 of 1

It is certified that error appears in the above-identified patent and that said Letters Patent is hereby corrected as shown below:

In the specification
Column 1, lines 15-20
Please correct the presentation of the "Statement of Government Grant" as follows:
This invention was made with government support under Grant No. AT003960 awarded by the
National Institutes of Health. The government has certain rights in the invention.

Signed and Sealed this
Nineteenth Day of July, 2016

Michelle K. Lee
*Director of the United States Patent and Trademark Office*